US007160857B2

(12) United States Patent
Tatton et al.

(10) Patent No.: US 7,160,857 B2
(45) Date of Patent: *Jan. 9, 2007

(54) METHODS FOR INCREASING SCHWANN CELL SURVIVAL

(76) Inventors: Nadine A. Tatton, 8 Halliday Ct., Purchase, NY (US) 10577; William G. Tatton, 8 Halliday Ct., Purchase, NY (US) 10577

( * ) Notice: Subject to any disclaimer, the term of this patent is extended or adjusted under 35 U.S.C. 154(b) by 447 days.

This patent is subject to a terminal disclaimer.

(21) Appl. No.: 10/104,709

(22) Filed: Mar. 22, 2002

(65) Prior Publication Data

US 2003/0004104 A1 Jan. 2, 2003

Related U.S. Application Data

(63) Continuation of application No. 09/170,460, filed on Oct. 13, 1998, now Pat. No. 6,417,160.

(60) Provisional application No. 60/074,448, filed on Feb. 12, 1998, provisional application No. 60/062,409, filed on Oct. 14, 1997.

(51) Int. Cl.
*A61K 38/18* (2006.01)
*A61K 31/445* (2006.01)
*A61K 31/40* (2006.01)
*A61K 31/198* (2006.01)
*C07K 14/65* (2006.01)

(52) U.S. Cl. .............................. 514/12; 514/2; 514/317; 514/408; 514/562; 514/649

(58) Field of Classification Search .................... 514/2, 514/654; 530/300, 303
See application file for complete search history.

(56) References Cited

U.S. PATENT DOCUMENTS

| 4,522,811 | A |  | 6/1985 | Eppstein et al. ................ 514/2 |
| 5,374,548 | A |  | 12/1994 | Caras ......................... 424/450 |
| 5,399,331 | A |  | 3/1995 | Kasai et al. .................... 419/28 |
| 5,416,016 | A |  | 5/1995 | Low et al. ................. 435/240.1 |
| 5,444,095 | A | * | 8/1995 | Tatton et al. ................. 514/654 |
| 6,417,160 | B1 | * | 7/2002 | Tatton et al. ................... 514/2 |

FOREIGN PATENT DOCUMENTS

| WO | WO 92/17169 | 10/1992 |
| WO | WO 9325219 | 12/1993 |
| WO | WO 97/28791 | 8/1997 |
| WO | WO 97/33572 | 9/1997 |

OTHER PUBLICATIONS

Apfel, et al. (1993)The Use of Insulin-Like Growth Factor I in the Prevention of Vincristine Neuropathy in Mice, *AN. N. Y. ACAD. SCI.*, 692:243-245.

Berge, S.M. et al. "Pharmaceutical Salts" *Journal of Pharmaceutical Sciences* 66(1):1-19 (1977).

Bernheimer, H. et al. "Brain Dopamine and the Syndromes of Parkinson and Huntington Clinical, Morphological and Neurochemical Correlations" *Journal of the Neurological Sciences* 20:415-455 (1973).

Birkmayer, W. et al. "(-)-Deprenyl Leads to Prolongation of L-Dopa Efficacy in Parkinson's Disease" *Mod. Probl. Pharmacopsychiat.* 19:170-176 (1983).

Birkmayer, W. and Riederer, P. "Deprenyl Prolongs the Therapeutic Efficacy of Combined L-DOPA in Parkinson's Disease" *Advances in Neurology* 40:475-481 (1984).

Birkmayer, W. et al. "Increased Life Expectancy Resulting from Addition of L-Depmyl to Madopar® Treatment in Parkinson's Disease: A Longterm Study" *Journal of Neural Transmission* 64:113-127 (1985).

Birkmayer, W. et al. "The Potentiation of the Anti Akinetic Effect after L-Dopa Treatment by and Inhibitor of Mao-B, Deprenil" *Journal of Neural Transmission* 36:303-326 (1975).

Bloemen, P.G.M. et al. "Adhesion Molecules: A New Target for Immunoliposome-mediated Drug Delivery" *FEBS Letters* 357:140-144 (1995).

Briscoe, P. et al. "Delivery of Superoxide Dismutase to Pulmonary Epithelium via pH-Sensitive Liposimes" *Am. J. Physiol.* 268:L374-L380 (1995).

Cedarbaum, J.M. et al. "A Double-blind Crossover Comparison of Sinemet CR4 and Standard Sinemet 25/100 in Patients with Parkinson's Disease and Fluctuating Motor Performance" *Journal of Neurology, Neurosurgery, and Psychiatry* 52:207-212 (1989).

Conn's current therapy, Rankel, R.E. Editor, W.B. Sauders Company, A Division of Harcourt Brace & Company Philadelphia, USA pp. 489-490 (1989).

Elizan, T.S. et al. "Selegiline as and Adjunct to Conventional Levodopa Therapy in Parkinson's Disease" *Arch. Neurol.* 46:1280-1283 (1989).

Fischer, P.-A. and Baas, H. "Therapeutic Efficacy of R-(—)-deprenyl as Adjuvant Therapy in Advanced Therapy in Advanced Parkinsonism" *J. Neural. Transm.* 25(Suppl.):137-147 (1987).

Golbe, L.I. "Long-term Efficacy and Safety of Deprenyl (Selegiline) in Advanced Parkinson's Disease" *Neurology* 39:1109-1111 (1989).

Golbe, L.I. et al. "Selegiline and Parkinson's Disease—Protective and Symptomatic Considerations" *Drugs* 39(5):646-651 (1990).

(Continued)

*Primary Examiner*—B. Dell Chism
(74) *Attorney, Agent, or Firm*—Lahive and Cockfield, LLP; Elizabeth A. Hanley, Esq.; Cynthia M. Soroos, Esq.

(57) ABSTRACT

Methods for increasing Schwann cell survival are disclosed. The methods of the invention are useful for the treatment of conditions such as peripheral neuropathies, including diabetic neuropathies.

26 Claims, 12 Drawing Sheets

OTHER PUBLICATIONS

Ishii, D.N., et al. (1995)"Insulin-Like Growth Factors Protect Against Diabetic Neuropathy: Effects on Sensory Nerve Regeneration in Rats", Journal of Neurosciece Rsearch, 40(1):138-144.

Keinänen and Laukkanen, M-L. "Biosynthetic Lipid-tagging of Antibodies" *FEBS Letters* 346:123-126 (1994).

Killion, J.J. and Fidler, I.J. "Systemic Targeting of Liposome-Encapsulated Immunomodulators to Macrophages for Treatment of Cancer Metastasis" *Immunomethods* 4:273-279 (1994).

Lieberman, A.N. et al. "Deprenyl Versus Placebo in Parkinson Disease: A Double-blind Study" *New York State Journal of Medicine* 87:646-649 (1987).

Love, et. al. (1996)"Effects of the sulfhydryl donor NAC on nerve conduction, perfusion, maturation and regeneration following freeze damage in diabetic rats", *European Journal of Clinical investigation*, 26(8):698-706.

Morgenlander, J.C. "Recognizing Peripheral Neuropathy—How to Read the Clues to an Underlying Cause" *Postgraduate Medicine* 102(3):71-80 (1997).

Owais, M. et al. "Chloroquine Encapsulated in Malaria-Infected Eryghrocyte-Specific Antibody-Bearing Liposomes Effectively Controls Chloroquine-Resistant *Plasmodium berghei* Infections in Mice" *Antimicrobial Agents and Chemotherapy* 39(1); 180-184 (1995).

Parkinson Study Group "DATATOP: A Multicenter Controlled Clinical Trial in Early Parkinson's Disease" *Arch. Neurol.* 46:1052-1060 (1989).

The Parkinson Study Group "Effect of Deprenyl on the Progression of Disability in Early Parkinson's Disease" *New England Journal of Medicine* 321:1364-1371 (1989).

Ranade, V.V. "Drug Delivery Systems. 1. Site-Specific Drug Delivery Using Liposomes as Carriers" *J. Clin. Pharmacol.* 29:685-694 (1989).

Rideout, et al. (1997)"High Glucose Induced Apoptosis Of Schwann Cells Is Prevented By IGF-1 and (-) Desmehydeprenyl", *Soc. for Neurosci. Abstr.*, 23(1-2): 65.

Sagara, et al. (1996)"Inhibition of peripheral neuropathy in streptoxotocin-induced diabetic rats with NAC", *Diabetologia*, 39(3):263-269.

Schiller, J.H. et al. "Amifostine, Cisplatin, and Vinblastine in Metastatic Non-Small-Cell Lung Cancer: A Report of High Response Rates and Prolonged Survival" *Journal of Clinical Obcology* 14(6):1913-1921 (1996).

Schreier, H. et al. "Targeting of Liposomes to Cells Expressing CD4 Using Glycosylphosphatidylinositol-anchored gp120" *The Journal of Biological Chemistry* 269(12):9090-9098 (1994).

Sondell, et. al. (1997)The IGF I In The Prevention Of Vincristine, *Neuroreport*, 8(13):2871-2876.

Stedman's medical dictionary, $26^{th}$ ed. Williams & Wilkins, a Waverly Co. p. 305(1995).

Tabernero, A., et al. (1996)"IGFs Exert a Positive Effect On Both the Proliferation and Differentiotion of Rat Schwann cells in culture", *Journal of Physiology*, 493:162s.

Umezawa, F. and Eto, Y. "Liposome Targeting to Mouse Brain: Mannose as a Recognition Marker" *Biochemical and Biophysical Research Communications* 153(3):1038-1044 (1988).

Veldhuis, G.J. et al. "Paclitaxel, Ifosfamide and Cisplatin with Granulocyte Colony-stimulating Factor or Recombinant Human Interleukin 3 and Granulocyte Colony-stimulating Factor in Ovarian Cancer: A Feasibility Study" *British Journal of Cancer* 75(5):703-709 (1997).

Zhuang, et al. (1996)"IGFs Reverse or Arrest Diabetic Neuropathy", *Experimental Neurology*, 140:198-205.

\* cited by examiner

Figure 3 - Appearance of PD2 Schwann Cells Exposed to 40 mM Glucose for 24 hr

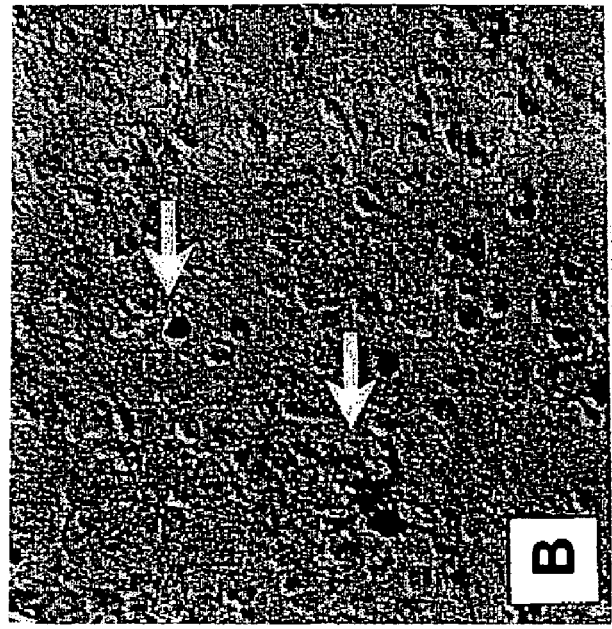
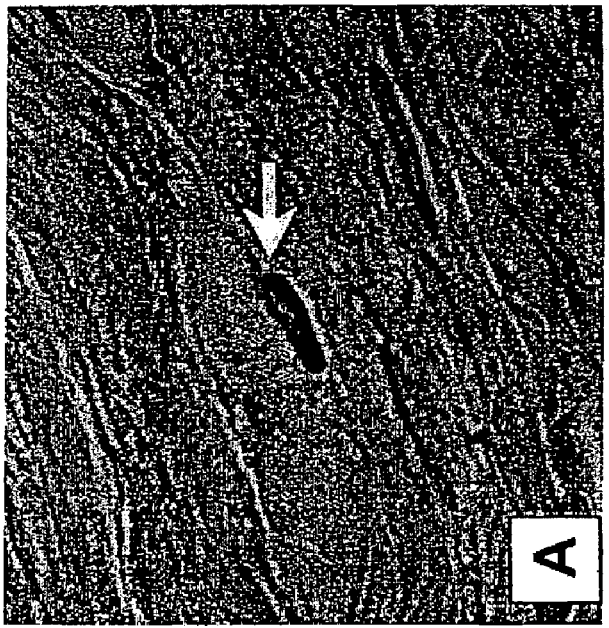
A. ApopTag positive Schwann cell in diabetic rat sciatic nerve.
B. ApopTag positive neurons in PD4 kitten brain.
Figure 11

METHODS FOR INCREASING SCHWANN CELL SURVIVAL

RELATED APPLICATIONS

This application is a continuation application of application Ser. No. 09/170,460 filed on Oct. 13, 1998 now U.S. Pat. No. 6,417,160.

This application claims the benefit of priority under 35 U.S.C. 119(e) to U.S. Provisional Application No(s). 60/062,409, filed on Oct. 14, 1997, and 60/074,448, filed on Feb. 12, 1998, the entire contents of which are hereby incorporated by reference.

BACKGROUND OF THE INVENTION

Deprenyl (also referred to herein as selegiline or R-(−)-N,α-Dimethyl-N-2-propynyl phenethylamine) was first used as an adjunct to conventional drug therapy (L-dihydroxyphenylalanine (L-DOPA) plus a peripheral decarboxylase inhibitor) of Parkinson's disease (PD) in Europe over a decade ago on the basis that as a selective monoamine oxidase-B (MAO-B) inhibitor, it would elevate brain dopamine levels and potentiate the pharmacologic action of dopamine formed from L-DOPA, and yet prevent the tyramine-pressor effect observed with non-selective MAO inhibitors. The combined drug therapy was reported to prolong the anti-akinetic effects of L-DOPA, resulting in the disappearance of on-off effects, reduced functional disability, and increased life-expectancy in PD patients (Bernheimer, H., et al., J. Neurolog. Sci., 1973. 20: 415–455, Birkmayer, W., et al., J. Neural Transm., 1975. 36:303–336, Birkmayer, W., et al., Mod. Prob. Pharmacopsychiatr., 1983. 19: 170–177, Birkmayer, W. and P. Riederer, Hassler, R. G. and J. F. Christ (Ed.) Advances In Neurology, 1984. 40(Y): p. 0–89004, and Birkmayer, W., et al., J. Neural Transm., 1985. 64(2): p. 113–128).

Studies examining deprenyl as an adjunct to conventional L-DOPA therapy have reported a short term benefit which was usually lost by 1 year or less. Some, but not all, have reported that the levodopa dose can be decreased when taken in conjunction with deprenyl (Elizan, T. S., et al., Arch Neurol, 1989. 46(12): p. 1280–1283, Fischer, P.A. and H. Baas, J. Neural Transm. (suppl.), 1987.25: p. 137–147, Golbe, L. I., Neurology, 1989.39: p. 1109–1111, Lieberman, A. N. et al., N.Y. State J. Med., 1987. 87: p. 646–649, Poewe, W., F. Gerstenbrand, and G. Ransomayr, J. Neural Transm. (suppl.), 1987. 25: p. 137–147, Cedarbaum, J. M., M. Hoey, and F. H. McDowell, J. Neurol. Neurosurg. Psychiatry, 1989. 52(2): p. 207–212, and Golbe, L. I., J. W. Langston, and I. Shoulson, Drugs, 1990. 39(5): p. 646–651).

Increasingly, deprenyl is being administered to Parkinson's disease patients following reports (Parkinson, S. G. Arch Neurol 46, 1052–1060 (1989) and U.S.A., Parkinson, S. G. N. Engl. J. Med. 321, 1364–1371 (1989)) that it delays the disease progression; a mechanism has recently been proposed to explain its action (See, e.g., Tatton & Redman 1996).

Peripheral neuropathy is art-recognized and is a common neurological disorder resulting from damage to the peripheral nerves. It is a condition which is associated with several underlying conditions, including conditions such as inheritable neuropathies, diabetes, rheumatoid arthritis, acquired immunodeficiency syndrome (AIDS) and thyroid disease or associated side-effect of anti-cancer therapy, i.e., cisplatin treatment (see J. Clinical Oncology 14(6):1913 (1996), B. J Cancer 75(5):703 (1997) (for a review, see, e.g., Morgenlander, J.C., Postgrad. Med. (1997) 102 (3): 71, and references cited therein).

Peripheral neuropathies can be debilitating, and treatment of such neuropathies is often difficult. Accordingly, methods of inhibiting or preventing the progression of peripheral neuropathies are needed.

SUMMARY OF THE INVENTION

It has now been discovered that certain compounds are capable of increasing survival of Schwann cells. The invention provides methods for increasing survival of Schwann cells both in vivo and in vitro, of preventing or inhibiting death of Schwann cells, of preventing or inhibiting the progression of peripheral neuropathy, and methods for treating a peripheral neuropathy.

In one aspect, the invention provides a method for increasing survival of Schwann cells. The method comprises administering to a subject in need thereof an effective amount of a compound selected from the group consisting of a deprenyl compound, N-acetylcysteine, and an insulin-dependant growth factor (IGF), such that survival of Schwann cells is increased. In certain embodiments, the deprenyl compound is represented by the structure:

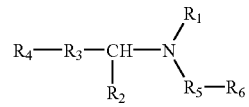

in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alky;

$R_3$ is a single bond, alkylene, or —$(CH_2)_n$—X—$(CH_2)_m$;
in which X is O, S, or N-methyl; m is 1 or 2; and n is 0, 1, or 2;

$R_4$ is alkyl, alkenyl, alkynyl, heterocyclyl, aryl or aralkyl; and $R_5$ is alkylene, alkenylene, alkynylene and alkoxylene; and $R_6$ is $C_3$–$C_6$ cycloalkyl or —C≡CH; or $R_2$ and $R_4$–$R_3$ are joined to form, together with the methine to which they are attached, a cyclic or polycyclic group;

and pharmaceutically acceptable salts thereof. In certain embodiments: $R_1$ is a group that can be removed in vivo; $R_1$ is hydrogen; $R_1$ is alkyl; $R_1$ is methyl; $R_2$ is methyl; $R_3$ is methylene; wherein $R_4$ is aryl; $R_4$ is phenyl; $R_5$ is methylene; $R_6$ is

—C≡CH.

In certain preferred embodiments, the deprenyl compound is represented by the structure:

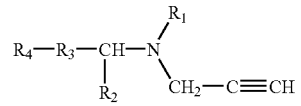

in which

R₁ is hydrogen, alkyl, alkenyl, alkynyl, aralkyl, alkylcarbonyl, arylcarbonyl, alkoxycarbonyl, or aryloxycarbonyl;

R₂ is hydrogen or alkyl;

R₃ is a bond or methylene; and

R₄ is aryl or aralkyl; or

R₂ and R₄–R₃ are joined to form, together with the methine to which they are attached, a cyclic or polycyclic group;

and pharmaceutically acceptable salts thereof.

In certain preferred embodiments, the deprenyl compound is represented by the structure:

$$R_4-R_3-CH-N\begin{matrix}CH_3\\ \\R_5-C\equiv CH\end{matrix}$$
$$\phantom{R_4-R_3-C}|\phantom{H-N}$$
$$\phantom{R_4-R_3-C}R_2\phantom{H-N}$$

in which

R₂ is hydrogen or alkyl;

R₃ is a bond or methylene; and

R₄ is aryl or aralkyl; or

R₂ and R₄–R₃ are joined to form, together with the methine to which they are attached, a cyclic or polycyclic group; and R₅ is alkylene, alkenylene, alkynylene and alkoxylene;

and pharmaceutically acceptable salts thereof.

In certain preferred embodiments, the deprenyl compound is represented by the structure:

<chemical structure: phenyl ring with substituent A_n, connected to –CH₂–CH(CH₃)–N(R₁)–CH₂–C≡CH> in which

R₁ is hydrogen, alkyl, alkenyl, alkynyl, aralkyl, alkylcarbonyl, arylcarbonyl, alkoxycarbonyl, or aryloxycarbonyl;

A is a substituent independently selected for each occurence from the group consisting of halogen, hydroxyl, alkyl, alkoxyl, cyano, nitro, amino, carboxyl, —CF₃, or azido;

n is 0 or an integer from 1 to 5;

and pharmaceutically acceptable salts thereof.

In certain preferred embodiments, the patient is a human. In a partiularly preferred embodiment, the deprenyl compound is (-)-desmethyldeprenyl.

In another aspect, the invention provides a method for inhibiting peripheral neuropathy, comprising administering to a patient an effective amount of a compound selected from the group consisting of a deprenyl compound, N-acetyl cysteine and IGF-1, such that peripheral neuropathy is inhibited. In a preferred embodiment, the deprenyl compound is (-)-desmethyldeprenyl. In certain embodiments, the neuropathy is selected from the group consisitng of diabetic neuropathy and AIDS-related neuropathy. In certain embodiments, the patient is a human.

In another aspect, the invention provides a method for increasing Schwann cell survival in vitro, comprising contacting Schwann cells with an effective amount of a compound selected from the group consisiting of a deprenyl compound, N-acetyl cysteine and IGF-1, such that Schwann cell survival is increased.

In another aspect, the invention provides a method for increasing Schwann cell survival in a patient, comprising contacting a Schwann cell with a compound selected from the group consisting of a deprenyl compound, N-acetyl cysteine and IGF-1, such that Schwann cell survival increases. In preferred embodiments, the patient is a human; the deprenyl compound is (-)-desmethyldeprenyl; and/or the (-)-desmethyldeprenyl is administered transdermally to the patient.

In another aspect, the invention provides a composition comprising N-acetylcysteine in a pharmaceutically acceptable carrier.

BRIEF DESCRIPTION OF THE DRAWING

FIG. 8 presents confocal laser microscopic images of CMTMR dye in PD2 cells after 6hr exposure in each of the listed media, illustrating the effect of DMD and cyclosporin A in preventing ΔΨM drop.

FIG. 11 shows in situ end-labeled nuclei from cryosections through the sciatic nerve and (control) brain cells, as further detailed in Example 2.

DETAILED DESCRIPTION OF THE INVENTION

Figure 1:
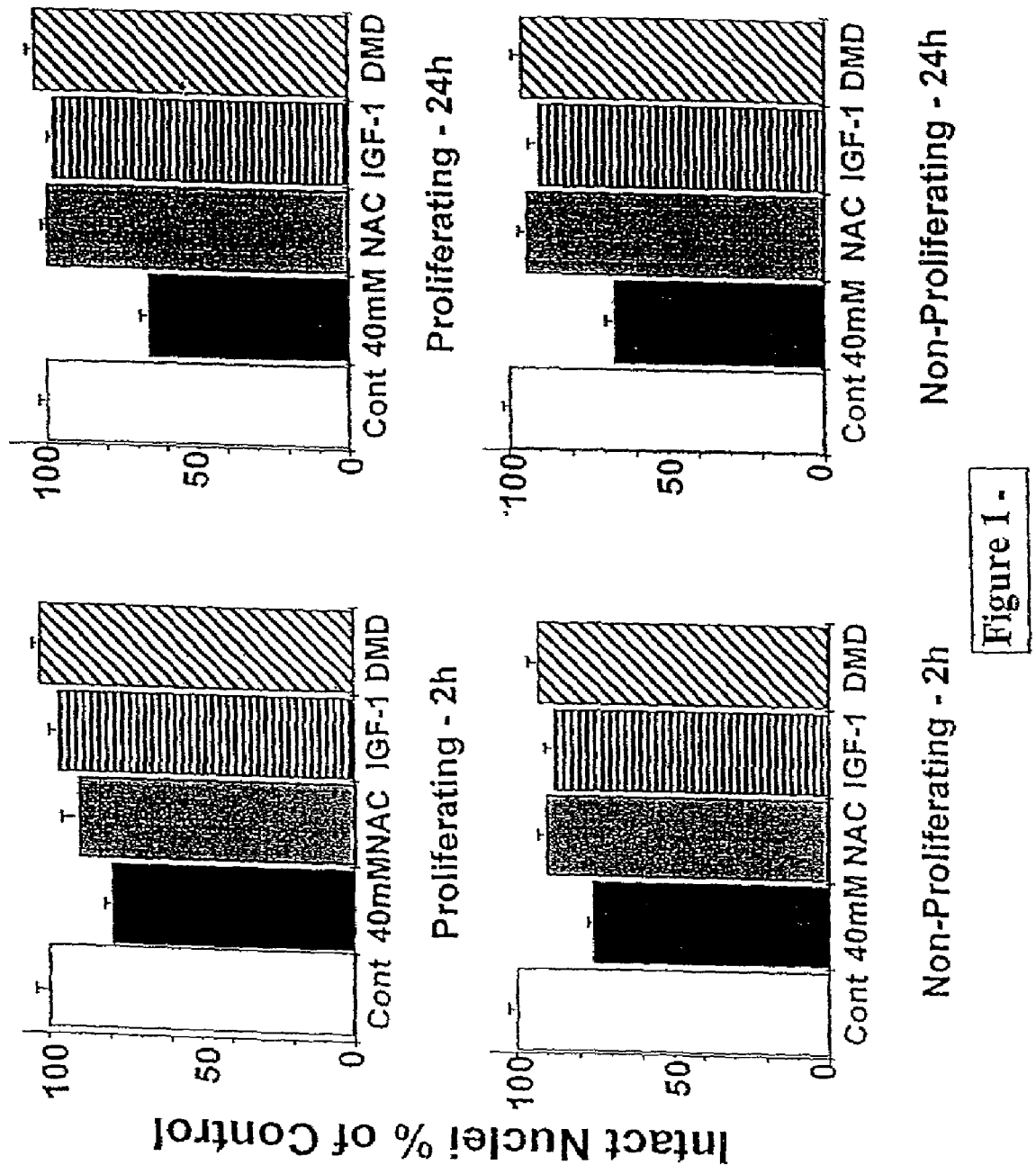
FIG. 1 is a set of bar graphs showing the effect of (-)-desmethyldeprenyl on survival of Schwann cells in cell culture under several conditions.

The present invention provides methods for increasing Schwann cell survival in a patient or in vitro, or for treating a peripheral neuropathy in a subject suffering from, or susceptable to, a peripheral neuropathy.

The terms "patient" or "subject", as used herein, refer to a warm-blooded animal having damaged damaged glial and/or Schwann cells, or suffering from or susceptable to Schwann cell damage or death, or suffering from or susceptible to a peripheral neuropathy. In preferred embodiments, the patient is a mammal, including humans and non-human mammals such as dogs, cats, pigs, cows, sheep, goats, rats, and mice. In a particularly preferred embodiment, the patient is a human. In certain embodiments, the patient is suffering from a condition associated with peripheral neuropathy, including, but not limited to, diabetes, AIDS, rheumatoid arthritis, or a thyroid disease. Drug-induced neuropathy is also associated with certain therapeutic regimes (such as administration of cis-platin); the invention also provides methods for Preventing or treating such drug-induced conditions. The methods of the invention are also useful for preventing or slowing the onset of a peripheral neuropathy or a symptom or condition associated therewith in a patient not yet suffering from a peripheral neuropathy, but susceptable to the development of a peripheral neuropathy (e.g., a diabetic subject). Thus, prophylactic administration of a deprenyl compound, N-acetylcysteine, or TGF-1 can inhibit Schwann cell death or development of a peripheral neuropathy in a patient who would otherwise be susceptible to such a condition.

The term "rescue of damaged Schwann cells" or "rescuing of damaged glial cells" herein refer to the reversal of the sequence of damage to death in (otherwise) lethally damaged Schwann (or glial) cells (e.g., caused by concentrations of glucose which can cause Schwann cell death). In certain embodiments, "rescue of damaged Schwann cells includes prevention of apoptosis in a Schwann cell.

The language "increasing survival of Schwann cells" as used herein, refers to increasing numbers of Schwann cells, preventing death of Schwann cells, or otherwise increasing numbers of Schwann cells (proliferating or non-proliferating), either in vitro (e.g., in cell culture) or in a subject.

The language "inhibiting peripheral neuropathy" as used herein, refers to preventing, slowing or reversing the development of peripheral neuropathy, or a symptom or condition associated therewith. For example, administration of a compound to a subject to inhibit peripheral neuropathy includes administering a compound such that progression of a peripheral neuropathy is prevented, slowed, or reversed, in whole or in part, or at least one symptom (or development of a symptom) is prevented, slowed, reversed, or otherwise ameliorated.

It is known that deprenyl and deprenyl compounds can resucue, or prevent the death of, damaged nerve cells (see, e.g., U.S. Pat. No. 5,444,095 and International Publication No. WO 97/28791, incorporated herein by reference). However, it is belived that the use of deprenyl or deprenyl compounds to increase the survival of Schwann cells, or to rescue, or prevent the death of, Schwann cells, has not previously been reported.

The methods of the invention find use in treatment of conditions associated with peripheral neuropathy, as well as in cell culture. For example, as described in Example 1, infra, high glucose concentrations can cause death of Schwann cell under conditions of high glucose concentration, either in vivo (e.g., in a subject suffering from diabetes or another condition associated with high levels of glucose, e.g., high blood glucose levels) or in vitro, e.g., in cell culture.

I. Deprenyl Compounds

The language "deprenyl compound", as used herein, includes deprenyl (N,α-dimethyl-N-2-propynylphenethylamine), compounds which are structurally similar to deprenyl, e.g., structural analogs, or derivatives thereof. Thus, in one embodiment, a deprenyl compound can be represented by the following formula (Formula I):

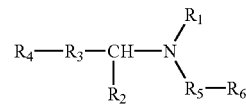

Formula I in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a single bond, alkylene, or —$(CH_2)_n$—X—$(CH_2)_m$;

in which X is O, S, or N-methyl; m is 1 or 2; and n is 0,1, or 2;

$R_4$ is alkyl, alkenyl, alkynyl, heterocyclyl, aryl or aralkyl; and $R_5$ is alkylene, alkenylene, alkynylene and alkoxylene; and R6 is $C_3$–$C_6$ cycloalkyl or —C≡CH; or $R_2$ and $R_4$–$R_3$ are joined to form, together with the methine to which they are attached, a cyclic or polycyclic group;

and pharmaceutically acceptable salts thereof.

In certain preferred embodiments, a deprenyl compound is not selected from the group consisting of deprenyl, pargyline, AGN-1133, AGN-1135, or MD 240928.

In preferred embodiments, $R_1$ is a group that can be removed in vivo. In certain embodiments, $R_1$ is hydrogen. In other preferred embodiments, $R_1$ is methyl. In certain preferred embodiments, $R_2$ is hydrogen. In certain preferred embodiments, $R_2$ is methyl. In some preferred embodiments, $R_3$ is alkylene, more preferably methylene. In other preferred embodiments, $R_3$ is —$(CH_2)_n$—X—$(CH_2)_m$. In preferred embodiments, $R_4$ is aryl. In certain preferred embodiments, $R_4$ is phenyl. In other preferred embodiments, $R_4$ is aralkyl. In yet other preferred embodiments, $R_4$ is alkyl. In still other preferred embodiments, $R_5$ is alkylene, more preferably methylene. In certain preferred embodiments, $R_6$ is

—C≡CH.

In other preferred embodiments, $R_6$ is cyclopentyl.

In another preferred embodiment, the deprenyl compound has the structure

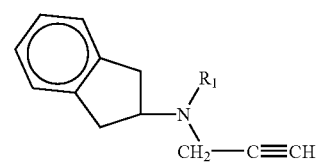

wherein $R_1$ is as described above. Preferred deprenyl compounds include (−)-desmethyldeprenyl, and

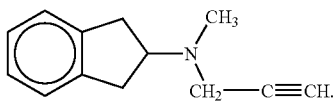

In another embodiment, a deprenyl compound can be represented by the following formula (Formula II):

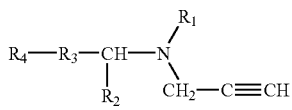

Formula II in which

R₁ is hydrogen, alkyl, alkenyl, alkynyl, aralkyl, alkylcarbonyl, arylcarbonyl, alkoxycarbonyl, or aryloxycarbonyl;

R₂ is hydrogen or alkyl;

R₃ is a bond or methylene; and

R₄ is aryl or aralkyl; or

R₂ and R₄–R₃ are joined to form, together with the methine to which they are attached, a cyclic or polycyclic group;

and pharmaceutically acceptable salts thereof.

In another embodiment, the deprenyl compound can be represented by the following formula (Formula III):

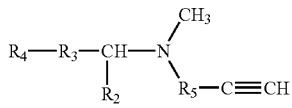

Formula III in which

R₂ is hydrogen or alkyl;

R₃ is a bond or methylene; and

R4 is aryl or aralkyl; or

R₂ and R₄–R₃ are joined to form, together with the methine to which they are attached, a cyclic or polycyclic group; and R₅ is alkylene, alkenylene, alkynylene and alkoxylene;

and pharmaceutically acceptable salts thereof.

In yet another embodiment, the deprenyl compound can be represented by the following formula (Formula IV):

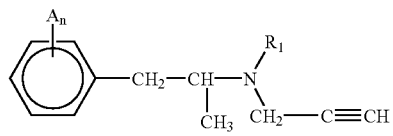

Formula IV in which

R₁ is hydrogen, alkyl, alkenyl, alkynyl, aralkyl, alkylcarbonyl, arylcarbonyl, alkoxycarbonyl, or aryloxycarbonyl;

A is a substituent independently selected for each occurence from the group consisting of halogen, hydroxyl, alkyl, alkoxyl, cyano, nitro, amino, carboxyl, —CF₃, or azido;

n is 0 or an integer from 1 to 5;

and pharmaceutically acceptable salts thereof.

In certain embodiments of the invention, the deprenyl compound is not deprenyl (including (−)-deprenyl).

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 20 or fewer carbon atoms in its backbone (e.g., $C_1$–$C_{20}$ for straight chain, $C_3$–$C_{20}$ for branched chain), and more preferably 10 or fewer. Likewise, preferred cycloalkyls have from 4–10 carbon atoms in their ring structure, and more preferably have 5, 6 or 7 carbons in the ring structure. Unless the number of carbons is otherwise specified, "lower alkyl" as used herein means an alkyl group, as defined above, but having from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —CF₃, —CN and the like. Exemplary substituted alkyls are described below. Cycloalkyls can be further substituted with alkyls, alkenyls, alkoxys, alkylthios, aminoalkyls, carbonyl-substituted alkyls, —CF₃, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group (e.g., an aromatic or heteroaromatic group). Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O-aryl. The term "acyloxy" refers to —O—C(O)—R₇, in which R₇ is alkyl, alkenyl, alkynyl, aryl, aralkyl or heterocyclyl.

The term "amino", as used herein, refers to —N(R₈)(R₉), in which R₈ and R₉ are each independently hydrogen, alkyl, alkyenyl, alkynyl, aralkyl, aryl, or R₈ and R₉, together with the nitrogen atom to which they are attached, form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N($R_8$)($R_9$), in which $R_8$ and $R_9$ are as defined above. The term "acylamino" refers to —N($R'_8$)C(O)—$R_7$, in which $R_7$ is as defined above and $R'_8$ is alkyl.

As used herein, the term "nitro" means —$NO_2$; the term "halogen" designates —F, —Cl, —Br or —I; the term "sulfhydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above for alkyls, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like. Aryl groups can also be part of a polycyclic group. For example, aryl groups include fused aromatic moieties such as naphthyl, anthracenyl, quinolyl, indolyl, and the like.

The terms "heterocyclyl" or "heterocyclic group" refer to 4- to 10-membered ring structures, more preferably 4- to 7-membered rings, which ring structures include one to four heteroatoms. Heterocyclyl groups include, for example, pyrrolidine, oxolane, thiolane, imidazole, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis.

The term "can be removed in vivo", as used herein, refers to a group that can be cleaved in vivo, either enzymatically or non-enzymatically. For example, amides can be cleaved by amidases, and N-methyl amines can be cleaved by enzymatic oxidation. For example, when deprenyl is administered to a subject, it is believed, as described infra, that the methyl group can be removed in vivo to yield an active compound. As a further example, with reference to Formula I, when $R_1$ is alkylcarbonyl, the resulting amide group can be hydrolytically cleaved in vivo, enzymatically or non-enzymatically, to yield a deprenyl compound including a secondary amine (e.g., $R_1$ is converted to hydrogen in vivo). Other groups which can be removed in vivo are known (see, e.g., R. B. Silverman (1992) "The Organic Chemistry of Drug Design and Drug Action", Academic Press, San Diego) and can be employed in compounds useful in the present invention.

II. Pharmaceutical Compositions

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject deprenyl compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The stability of deprenyl can be affected by the pH of the medium in which the deprenyl is formulated. For example, deprenyl is more stable at a pH in the range of about 3–5 than at a pH of about 7. Therefore, when formulating a deprenyl compound in a pharmaceutical composition, it is preferred that the deprenyl compound be maintained at a suitable pH. In preferred embodiments, a pharmaceutical composition of the invention has a pH in the range of about 3 to about 5, more preferably about 3 to about 4. Furthermore, ethyl alcohol is a preferred solvent for improving stability of deprenyl. Thus, in certain embodiments, alcoholic or aqueous alcoholic media are preferred for the pharmaceutical compositions of the invention.

As set out above, certain embodiments of the present deprenyl compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulfonate salts and the like (see, for example, Berge et al. (1977) "Pharmaceutical Salts", $J$ $Pharm.\ Sci.$ 66:1–19).

In other cases, the deprenyl compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the deprenyl compound which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent.

Methods of preparing these formulations or compositions include the step of bringing into association at least one deprenyl compound of the present invention with the carrier and, optionally, one or more accessory ingredients. In general, the formulations are prepared by uniformly and intimately bringing into association a deprenyl compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A deprenyl compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered deprenyl compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the deprenyl compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active deprenyl compound, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more deprenyl compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the deprenyl compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a deprenyl compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to a deprenyl compound of this invention, these substances. Sprays can additionally contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the deprenyl compound in the proper medium. Absorption enhancers can also be used to increase the flux of the deprenyl compound across the skin. The rate of such flux can be controlled by either providing a rate controlling membrane or dispersing the deprenyl compound in a polymer matrix or gel. Devices, including patches, which transdermally deliver a deprenyl compound by iontophoresis or other electrically-assisted methods can also be employed in the present invention, including, for example, the devices described in U.S. Pat. Nos. 4,708,716 and 5,372,579.

Ophthalmic formulations, eye ointments, powders, solutions, drops, sprays and the like, are also contemplated as being within the scope of this invention.

Pharmaceutical compositions of this invention suitable for parenteral administration comprise one or more deprenyl compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject deprenyl compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc.; administration by injection, infusion or inhalation; topical by lotion or ointment; and rectal by suppositories. Injection (subcutaneous or intraperitoneal) or topical ophthalmic administration are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular deprenyl compound of the present invention employed, or the ester, salt or amide thereof, the route of administration, the time of administration, the rate of excretion of the particular compound being employed, the duration of the treatment, other drugs, compounds and/or materials used in combination with the particular deprenyl compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a deprenyl compound of the invention will be that amount of the compound which is the lowest dose effective to produce a therapeutic effect. Such an effective dose will generally depend upon the factors described above. Generally, intraperitoneal and subcutaneous doses of the compounds of this invention for a patient, when used for the indicated nerve-cell rescuing effects, will range from about 0.0001 to about 10 mg per kilogram of body weight per day, more preferably from about 0.001 mg/kg to about 1 mg/kg per clay.

If desired, the effective daily dose of a deprenyl compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition). It will be understood that two or more deprenyl compounds can be administered in a single therapeutic composition.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

It is believed that certain deprenyl compounds can be at least partially metabolized in vivo after administration to a subject. For example, (−)-deprenyl can be metabolized by the liver to (−)-desmethyldeprenyl, as well as (−)-methamphetamine and (−)-amphetamine, after oral administration. The hepatic metabolism of (−)-deprenyl can be inhibited by administration of a $P_{450}$ inhibitor such as Proadifen. In animal and cell-culture studies, administration of Proadifen reduces the ability of (−)-deprenyl to prevent cell death, but does not block the cell-rescuing activity of (−)-desmethyldeprenyl. Thus, it is believed that at least one metabolite of (−)-deprenyl, most likely (−)-desmethyldeprenyl, is an active compound. It is presently believed that (−)-methamphetamine and (−)-amphetamine are inhibitors of the cell-rescuing activity of deprenyl compounds. It is also believed that monoamine oxidase (MAO, including both MAO-A and MAO-B) inhibitory activity is not required for nerve-cell rescuing activity. Absence of MAO inhibitor activity may in fact provide a drug with fewer side effects. Thus, in certain embodiments, it is preferred that the deprenyl compound have low MAO inhibitor activity, or be administered so as to minimize MAO inhibition (e.g., by use of a suitable prodrug or formulation).

In view of the foregoing, it is preferable to administer deprenyl compounds by a route that minimizes metabolism to inhibitor compounds such as (−)-methamphetamine and (−)-amphetamine, while allowing metabolism to active compounds such as (−)-desmethyldeprenyl. Metabolism to an active compound can occur at the desired site of activity, e.g., in the target organ or area, e.g., the brain. Thus, prodrugs, which are metabolized to active compounds, are useful in the methods of the invention.

It has been found that certain deprenyl compounds have greater therapeutic efficacy (e.g., are effective at lower doses) when administered so as to decrease or prevent the "first-pass" effect. Accordingly, intraperitoneal or especially subcutaneous injection are preferred routes of administration. In preferred embodiments, a deprenyl compound is administered in divided doses. For example, a deprenyl compound can be administered by frequent (e.g., pulsed) injections, or by a controlled infusion, which can be constant or programmably varied as described above. In preferred embodiments in which a deprenyl compound is administered orally, the deprenyl compound can be formulated to reduce the amount of hepatic metabolism after oral administration and thereby improve the therapeutic efficacy.

In certain embodiments, the deprenyl compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J Physiol.* 1233:134); gp120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In a preferred embodiment, the therapeutic compounds of the invention are formulated in liposomes; in a more preferred embodiment, the liposomes include a targeting moiety.

The invention is further illustrated by the following example, which should in no way be construed as being further limiting. The contents of all references, pending patent applications and published patent applications, cited throughout this application are hereby incorporated by reference. It should be understood that the animal models for nerve cell rescue used in the example are accepted and that a demonstration of efficacy in these models is predictive of efficacy in humans.

EXAMPLES

Example 1

Summary

Sensorimotor and autonomic neuropathies may be present in at least 40% of the diabetic population. Changes in nerve conduction velocity, abnormal remyelination, and a progressive clinical decline suggest that a 'normal' regenerative Schwann cell response to injury cannot or does not occur in the diabetic human. We have used primary cultures of postnatal day (PD) 2 and PD 15 Sprague Dawley rat Schwann cells isolated from sciatic nerve to examine the effects of elevated levels of D-glucose on glial cell survival and protein synthesis. Proliferating and non-proliferating rat Schwann cells were exposed to increasing glucose concentrations (5.5, 17.5, 30, 40 and 50 mM) for 48 hours. Counts of intact nuclei were used to quantitate cell survival at 2, 12, 24 and 28 hr. Dose-dependent cell death was observed for all elevated glucose media ($\geq 17$ mM) beginning at 2 hr. after exposure and continuing throughout the 48 hr. period. A maximum cell loss of 50% compared to control base media (5 mM glucose) occurred between 24–48 hr. In order to determine whether this cell death was apoptotic, we used in situ end-labeling (ISEL) with TdT and BODIPY FL-dUTP to tail free 3' -OH ends of DNA. We found an approximate 6 fold increase in the number of labeled nuclei after 12 exposure to 40 mM glucose compared to control values. Although counts of intact nuclei indicated significant cell loss after 2 hr. exposure to high glucose, ISEL did not reveal a significant increase in labeled nuclei compared to control, indicating that cell death at this time point was not apoptotic. We also found IGF-1, N-acetyl cysteine and desmethyldeprenyl added in a high glucose environment, could all significantly improve Schwann cell survival following 24 hr of high glucose exposure. For example, as shown in FIG. 1, (−)-desmethyldeprenyl (DMD in FIG. 1) is effective to prevent death of Schwann cells exposed to 40 mM glucose in cell culture. N-Acetylcysteine (NAC) and IGF-1 are also effective. These results demonstrate that high levels of glucose can cause Schwann cell pathology. Schwann cell pathology, due to prolonged exposure to hyperglycemic conditions, may thus be a contributing factor in the development of diabetic peripheral neuropathy. The protective effect of DMD demonstrates that deprenyl compounds can be useful in the treatment of diabetic peripheral neuropathy.

Materials and Methods

Schwann cells were obtained from postnatal day 2 (PD2) and postnatal day 15 (PD 15) rats.

Post-Natal Day 2 and Post-Natal Day 15 Schwann Cell Cultures

Litters from timed-pregnant Sprague-Dawley rats (Charles River, Montreal) were used at post-natal day 2 (PD2) or PD15. Following decapitation, the sciatic nerves were quickly removed and placed in an ice-cold base media of Dulbecco's modified Eagle's medium (DMEM, Sigma) containing 5.5 mM mM D-glucose, 25 mM HEPES, penicillin (20 U/ml) and streptomycin (20 µg/ml). The nerves were cut into 1 mm$^3$ segments and incubated in 0.0125% trypsin-EDTA/0.03% Type I collagenase in Hank's buffered salt solution (HBSS, Gibco) for 45 min at 37° C. The fragments were then washed in DMEM/10% fetal bovine serum (FBS, Gibco) and seeded onto 75 cm$^2$ tissue culture flasks (PD 15) or 25 cm$^2$ (PD2) (Nunc) coated with poly-L-lysine (Sigma). The cells were maintained at 37° C. in a 5% CO$_2$ atmosphere. Over the next 5 days, Schwann cells migrated out of the nerve pieces and adhered to the plastic surface. On day 5, the fragments were removed, and the remaining adherent cells maintained in DMEM/10% FBS with 500 µg/ml bovine pituitary extract (Upstate Biotechnology) and 0.5 µg/ml cholera toxin (Research Biochemicals) (PD2) or DMEM/10% FBS only (PD 15) until confluency was reached.

When confluent (day 10) the cells were harvested with 0.05% Trypsin-EDTA, and plated onto poly-L-lysine coated glass cover slips (12 mm, Carolina Biological Supply) at a density of 10,000 to 20,000 cells per cover slip, or onto poly-L-lysine coated 24 well plates (Nunc) for cell counting, at a density of 12,000 cells per well. Twenty-four hr after secondary plating, the medium was replaced with DMEM/ 5% FBS. Cells were allowed to stabilize in the new media for 48 hr. At this point, 0 hr, the cells were washed twice with serum-free DMEM and placed in DMEM/2% FBS supplemented with 5.5 mM (base medium), 17.5 mM, 30 mM, 40 mM, or 50 mM glucose. A second group of cells were maintained in DMEM/2% FBS and 40 mM glucose with or without IGF-1 (1 ng/ml), N-acetyl-L-cysteine (NAC, $10^{-7}$ M), or (−)-desmethyldeprenyl (DMD, $10^{-9}$ M).

Immunocytochemical Identification of Schwann Cells

Cells plated on cover slips were rinsed in phosphate buffered saline (PBS: 9 g NaCl, 3.2 g sodium phosphate monobasic, 10.9 g sodium phosphate dibasic/liter distilled H2O) and then fixed in ice-cold 4% paraformaldehyde for 10 min. After rinsing in PBS, cells were blocked in 10% normal goat serum or normal horse serum, followed by overnight incubation with primary antisera against: myelin associated glycoprotein (MAG; 1:20, Boehringer Mannheim), myelin basic protein (MBP; 1:100, Sternberger Monoclonals), CNPase (1:200, Sigma), L1 (1:20, Boehringer Mannheim), GFAP (1:800, Sigma), Thy 1.1 (hybridoma supernatant, ATCC), S100 (1:400, Dako), or ciliary neurotrophic factor (CNTF; 1:250, antiserum was kindly provided by Dr. Peter Richardson, Montreal General Hospital). Following a PBS rinse, cover slips were incubated with biotinylated secondary antibodies (1:300, Vector Labs) or FITC conjugated goat anti-rabbit IgG (1:250; Molecular Probes), TR conjugated goat anti-mouse IgG (1:200; Molecular Probes). Cover slips incubated with biotinylated secondary antibodies were rinsed in PBS, incubated for 30 min in avidin-horseradish peroxidase (Elite kit, Vector Labs) and then incubated with (1.2 mg/ml) diaminobenzidine (Sigma) mixed v:v with 0.01% hydrogen peroxide for chromogenic detection. Cover slips incubated with fluorescently labeled secondary antibodies were mounted in glycerol/PBS or Aquamount (BDH) and examined under epifluorescence with TR and FITC on a Leica true confocal scanning (TCS) microscope. Less than 5% of cells were positive for Thy 1.1 antiserum which detects fibroblasts.

Assessment of Schwann Cell Proliferation in Baseline Glucose Media

Post-natal day 2 and PD 15 Schwann cells grown in 24 well plates or on glass cover slips were maintained in the base medium containing 2% FBS and 5.5 mM glucose for the indicated time points (0, 2, 12, 24, and 48 hr). The cells were harvested and counts of intact nuclei (see below for description of counting method as applied to cell survival) were used to estimate proliferation. Additionally, Schwann cells grown on cover slips in base medium were fixed in 4% paraformaldehyde for 15 min and stained with an antibody raised against the Ki67 nuclear antigen. Cells that displayed no immunoreaction product were considered to be in the G$_0$ phase of the cell cycle and therefore not actively cycling. Cells in the G1-S phase showed Ki67 immunoreactivity associated with the nucleolus and in a few small patches throughout the nucleus, while cells in the G2-M phase displayed intense patches of immunoreactivity, as well as a range of Ki67 immunodensities in the nuclear matrix (Braun et al., 1988). Cells were counted in randomly determined grids created on a schematic of the 12 mm round cover slip. The random numbers were generated by the Microcal Origin™ software package and corresponded to coordinates representing individual 40× microscope fields. The numbers expressed represent the percentage of the total number of cells per grid in G$_0$, G$_1$, or G$_2$.

Assessment of Cell Survival in High Glucose Media

Cells were harvested at t=0, 2, 12, 24, and 48 hr after the addition of DMEM/2% FBS with varying glucose content (5.5 mM–50 mM). A second series of cells treated was treated with either 5.5 mM glucose or 40 mM glucose with the concomitant addition of IGF-1, DMD, or NAC and harvested at 24 hr. Cells were lightly digested with 0.25% trypsin-EDTA for 1 min, to remove them from the 24 well plates and the contents of each well centrifuged at 600×9 for 5 min. The supernatant was removed and the pelleted cells resuspended in 200 µl of lysis buffer containing 10% Zapoglobin (Coulter Electronics). Nuclei with a completely intact, smooth membrane enclosing visible nuclear material (under phase contrast microscopy) were counted on a haemocytometer. This counting method is effectively a sensitive measure of nuclear fragility. Mean values shown are taken from a minimum of 12 duplicate wells obtained from 3 or more litters.

Detection of Apoptotic Nuclei

In situ end labeling (ISEL) was used to detect free 3'-OH ends of endonuclease digested nuclear DNA, considered to be a characteristic feature of the degradative phase of apoptosis. Schwann cells grown on glass cover slips treated with 5.5, 17.5, or 40 mM glucose were fixed with cold 4% paraformaldehyde for 20 min at 2, 12, and 24 hr. Following a 1 min. permeabilization with methanol, the cover slips were treated with DNAse-free RNAse A (100 µml, Boehringer Mannheim) for 10 min at 37° C. Cover slips were then incubated with terminal deoxynucleotidyl transferase (TdT) reaction buffer (Boehringer Mannheim) for 15 min. Excess buffer was blotted away and replaced with fresh buffer containing 12.5 units TdT (Boehringer Mannheim) and 10 µM BODIPY-fluorescein-conjugated dUTP (Molecular Probes) for 60 min at 37° C. The reaction was terminated by several rinses with warm 2× SSC (0.03 M sodium citrate, 0.3 M sodium chloride). The cover slips were mounted in glycerol/PBS or Aquamount (BDH) and observed with a FITC filter on a Leica inverted microscope with epifluorescence. Using a 40× objective, cells in each of the 30 sample areas per cover slip showing evidence of nuclear apoptosis (round, bright green nucleus, pale cytoplasm) were counted. This procedure was repeated on 3 cover slips from each treatment.

The nucleic acid-specific cyanine dye YOYO-1 (Molecular Probes) was used to visualize chromatin condensation which is considered to be a characteristic feature of the end stage of apoptosis. Fixed cells were briefly permeabilized with methanol (−20° C.) for 30 sec and washed with PBS, followed by incubation with 1 mM YOYO-1 (diluted in PBS) at room temperature for 30 min. The cover slips were then washed several times with PBS and mounted in Aquamount for confocal imaging.

Confocal Imaging of Apoptotic Events

High-resolution laser confocal imaging techniques provide the opportunity to directly visualize the sub-cellular distribution of such proteins, allowing the reconstruction of the time course of pro-apoptotic signaling events. For example, treated cells can be labeled with the potentiometric dye CMTMR to provide an index of mitochondrial membrane potential ($\Delta\Psi M$) followed by immunocytochemical detection of proteins that may be sequestered in (e.g. BAX) or liberated from (e.g. BCL-2, p53, or cytochrome c) mitochondria during the early stages of apoptotic cell death. Subsequent analysis of corresponding confocal images within the same focal plane showing $\Delta\Psi M$ and the immunofluorescent signal of the particular protein at the same location within an individual mitochondria allow the estimation of the relationship between $\Delta\Psi M$ and the localization of specific proteins in mitochondria at specific points in the apoptotic signaling cascade. Such techniques have been employed in neuronally differentiated $PC_{12}$ cells to demonstrate that at high and medium levels of $\Delta\Psi M$ mitochondrial cytochrome c (CytC) and cytochrome c oxidase (subunit IV; COXIV) content do not correlate with $\Delta\Psi M$. However, at low $\Delta\Psi M$ levels, intramitochondrial CytC and COXIV levels fall dramatically and CytC and COXIV levels in adjacent cytoplasmic regions increase inversely. Epifluorescent microscopy cannot resolve many of these subcellular localization questions because of the background haze of fluorescence which results from those portions of the cell outside of the observed focal plane. Laser confocal imaging is based on the reduction of out of focus haze through the use of a series of pinholes of varying aperture which are placed in the path of the light exciting the sample and also, most importantly, in the path of emitted light coming from the sample. These pinholes dramatically reduce the contribution made by signals arising from out of focus elements to the final image. There is still, however, an appreciable amount of background "noise" in the confocal image that is not eliminated by the pinhole. This can be further reduced through the use of deconvolution algorithms that mathematically subtract the signal from above and below the optical plane of interest, resulting in a depth of resolution approaching 50 nm.

Analysis of Mitochondrial Membrane Potential ($\Delta\Psi M$)

As has been previously reported in a number of models of apoptosis, apoptotic cell death is often preceded by a fall in mitochondrial membrane potential ($\Delta\Psi M$). To determine if the observed Schwann cell death was also accompanied by a fall in $\Delta\Psi M$, Schwann cells from each of the groups (see below) were incubated with the potentiometric fluorescent dye, chloromethyl-tetramethylrhodamine methyl ester (CMTMR; Molecular Probes, 130 nM for 15 min at 37° C.). This dye is preferentially taken up by actively respiring mitochondria where it binds to protein thiol groups within the mitochondrial matrix and is retained following aldehyde fixation. The CMTMR fluorescence intensity therefore represents the highest level of negativity difference (i.e., the greatest $\Delta\Psi M$) in the mitochondria during the period of dye exposure prior to fixation.

A Leica true confocal scanning (TCS) microscope was used to image the cells. A pinhole aperture of 20 is maintained with constant laser and photo-detector power settings and an excitation filter wavelength of 488 nm and a bandpass emission filter of 600/30 nm. Each image was scanned using an oil-immersion, 100×, 1.4 N.A. objective at 512 by 512 by 8 bits per pixel resolution, background offset of −1 and line averaged 32 times. The confocal images were saved as grey-scale tagged image file format (TIFF) files for analysis and recolourization. The Metamorph™ (Universal Imaging, Ltd.) image capture and analysis system for Windows was used to measure the intensity of CMTMR fluorescence in individual mitochondria. In each mitochondrion, no fewer than two regions were defined by a box measuring 9 pixels square each. The average intensity per pixel within each defined region is measured and automatically logged to a Microsoft Excel spreadsheet for analysis.

In experiments where the localization and intensity of specific mitochondrial and other proteins (e.g., hexokinase, see above) are correlated with estimates of $\Delta\Psi M$, duplicate confocal images in the same focal plane are obtained for CMTMR and the immunofluorescence signal. For each of the defined CMTMR regions within mitochondria, the corresponding pixel coordinates are obtained using the Metamorph™ software package and the regions are then superimposed on the alternate immunofluorescence image. This has the advantage of permitting the measurement of the fluorescence intensity of the localized protein at the same location within the mitochondrion from which CMTMR intensity was measured and within the same focal plane.

To determine the relationship between a loss of $\Delta\Psi M$ and the mitochondrial localization of hexokinase (Type 1) with respect to apoptotic cell death, PD2 and PD15 Schwann cells were treated with 5.5 or 40 mM glucose in the presence or absence of agents that maintain the PTP in an open (atractyloside 1 mM) or closed (cyclosporin A, $10^{-7}$ M) state, or trophic withdrawal, for various time points. At the end of the indicated time point, Schwann cells so treated were incubated with CMTMR to estimate $\Delta\Psi M$, fixed with 4% paraformaldehyde, and processed for the immuncytochemical co-localization of hexokinase (Type 1) to mitochondria. The fixed coverslips were blocked for 1 hr with 10% normal donkey serum to minimize non-specific binding, and incubated with a mouse monoclonal antibody raised against hexokinase (Type 1; Chemicon) at a dilution of 1:500 overnight at 4° C. Coverslips were washed in PBS and incubated with a Cy5 conjugated donkey anti-mouse (Jackson Immuno Research) at a dilution of 1:250 for 1 hr at room temperature. Coverslips were then washed with PBS and mounted with Aquamount (BDH).

Results

Schwann Cell Survival and Proliferation in 5.5 mM Glucose Base Media

Figure 2:
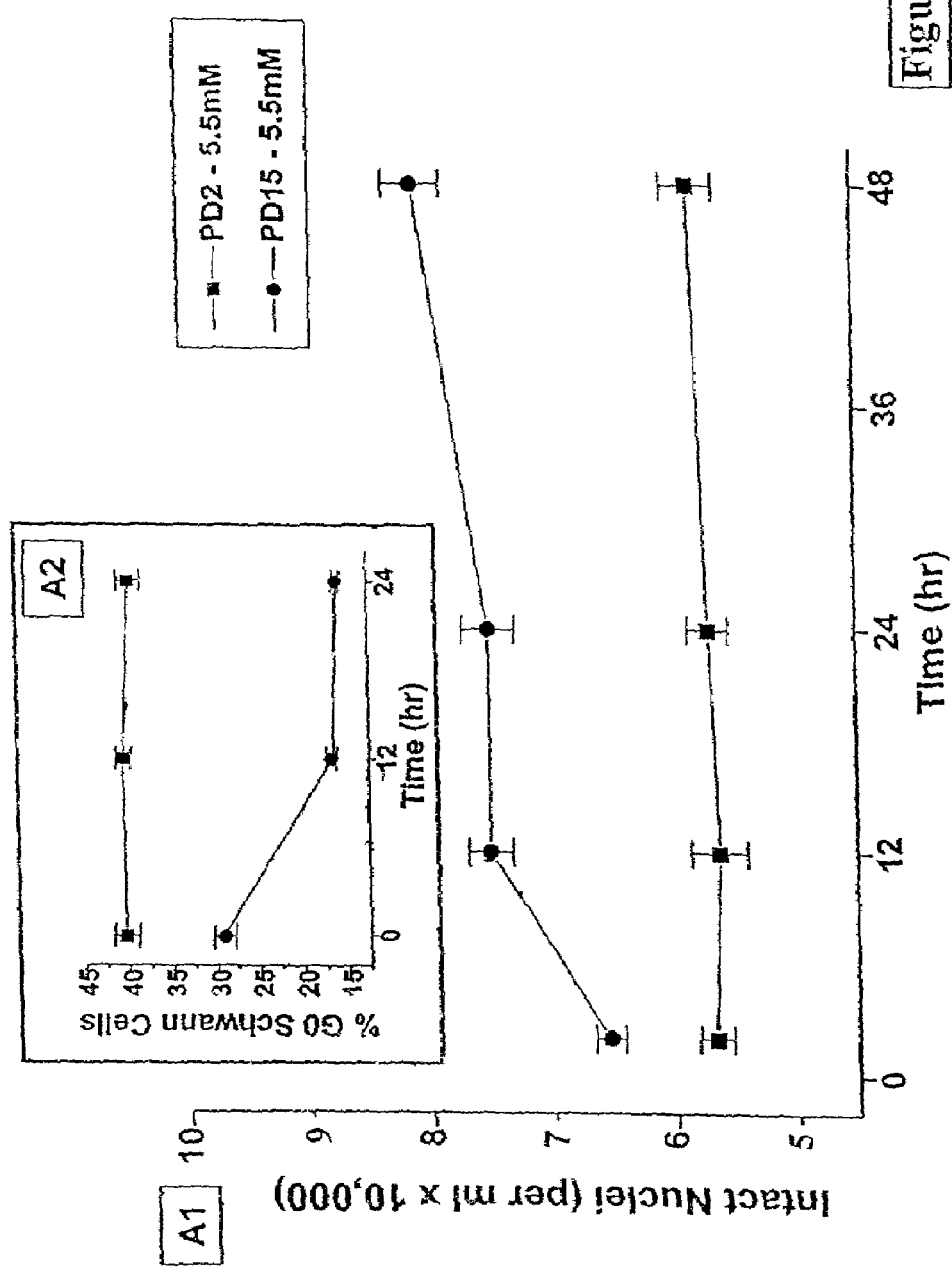
FIG. 2 illustrates the proliferation of PD2 and PD15 Schwann Cells as set forth in the Exemplification.

PD2 and PD 15 cells were also subcultured into 24 well plates in order to examine the effects of high glucose media on Schwann cell survival and proliferation. At 0 hr FBS was reduced from 5% to 2% in order to provide trophic maintenance levels of serum but not to stimulate proliferation. Counts of intact nuclei (n=12 wells) taken at 0, 12, 24 and 48 hr demonstrated that PD2 Schwann cells constituted a non-proliferating population when maintained in 5.5 mM glucose, while PD15 cells formed a proliferating population of cells with approximately a 1.2 fold increase in cell number by 48 hr (FIG. 2).

Identically treated cells on glass cover slips were incubated with antiserum to the Ki67 antigen and visualized via an immunoperoxidase method. Ki67 immunoreactivity is generally used prognostically to grade the histopathology of neoplasms. Cell nuclei which are immunonegative for Ki67 are considered to be in the $G_o$ phase of the cell cycle and thus have not entered the active (proliferative) phase of the cycle. The number of $G_o$ immunonegative cells were counted at 0, 12 and 24 hr for both PD2 and PD15 Schwann cells (see FIG. 2, inset). As would be predicted, for a non-proliferating population of cells (PD2) the number of cells in $G_o$ should stay constant, while for a proliferating population (PD 15), the percentage of cells remaining in $G_o$ should decline.

Figure 3:
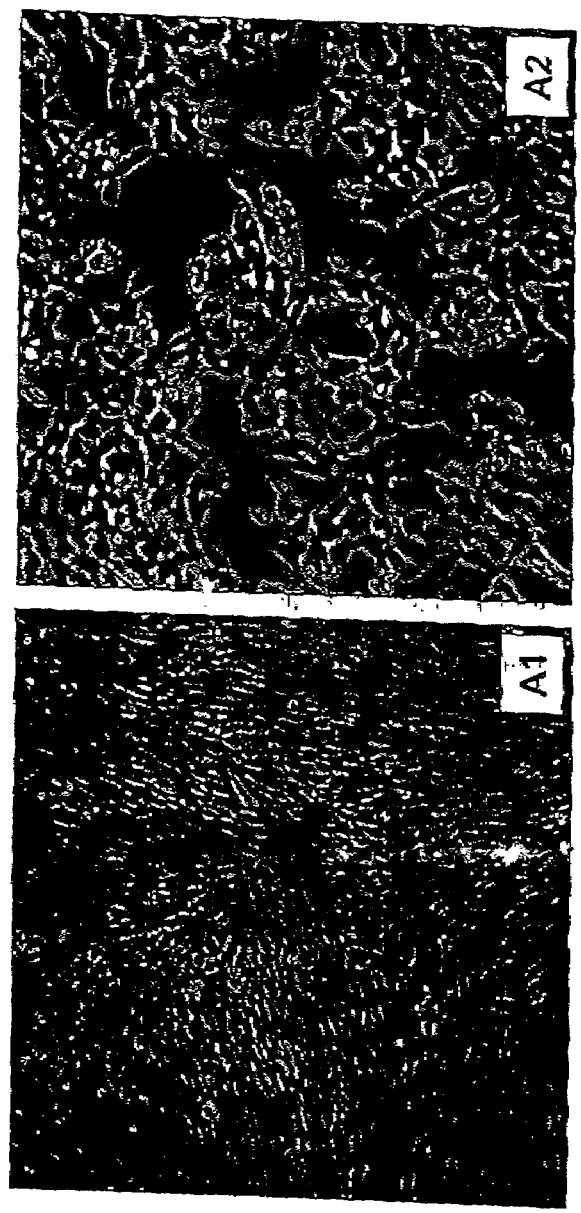
FIG. 3 is a phase contrast image of confluent PD2 Schwann cells at O hr in 5.5 mM glucose (base) media and after 24 hr in 40 mM glucose media.

Effects of High Glucose Media on "Proliferating" and "Non-Proliferating" Schwann Cells Schwann cells from PD2 and PD15 nerves were exposed to glucose concentrations ranging from 5.5 to 17.5, 30, 40 and 50 mM for a period of 48 hr. FIG. 3A1 is a phase contrast image of confluent PD2 Schwann cells at 0 hr in 5.5 mM glucose (base) media and after 24 hr in 40 mM glucose media (FIG. 3A2) showing obvious cell loss and an apparent 'rounding up' of some cells.

Figure 4:
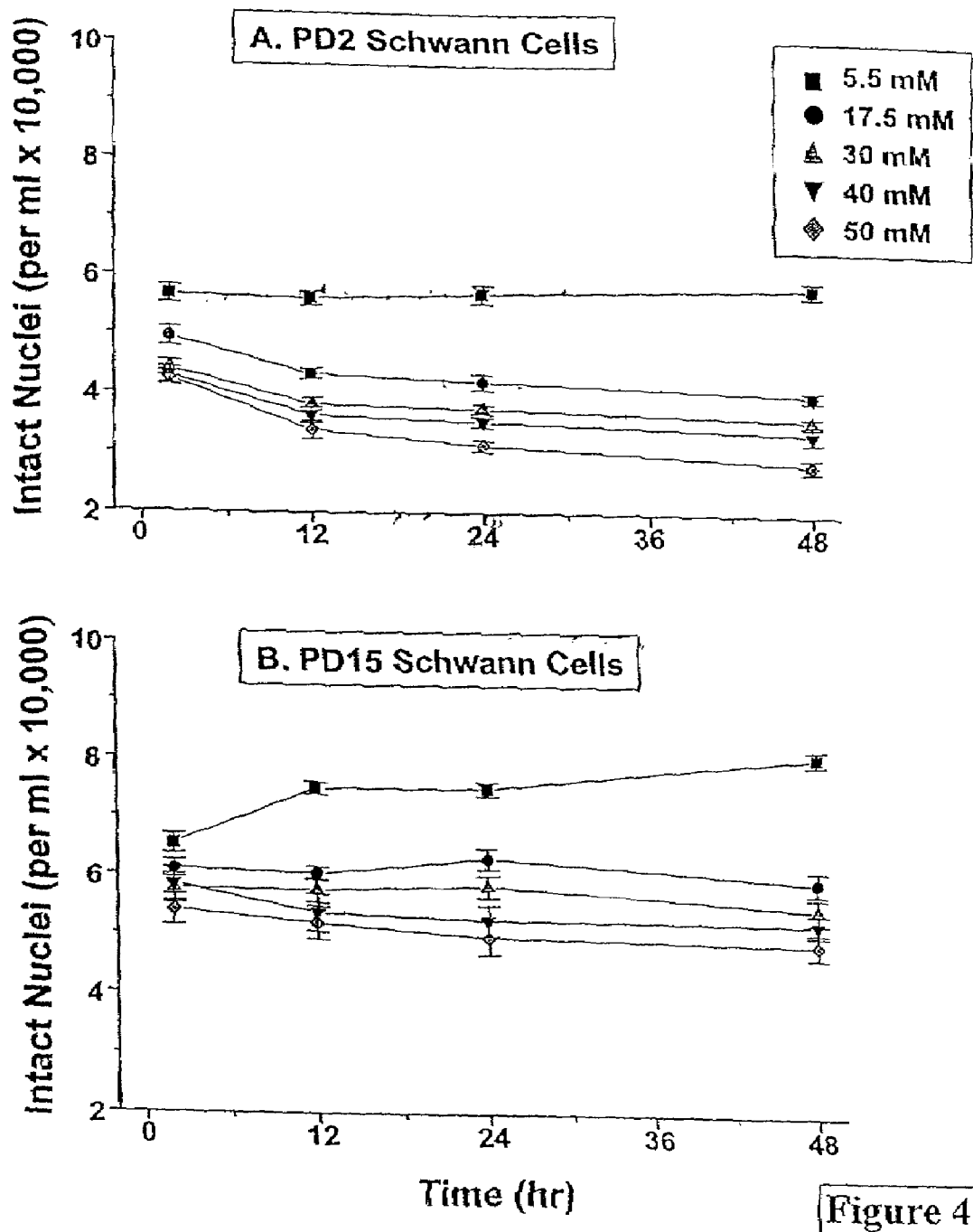
FIGS. 4 and 5 illustrate counts of intact PD2 and PD 15 Schwann cell nuclei following exposure to 5.5, 17.5, 30, 40 and 50 mM glucose media at 0, 2, 12, 24 and 48 hr.
Figure 5:
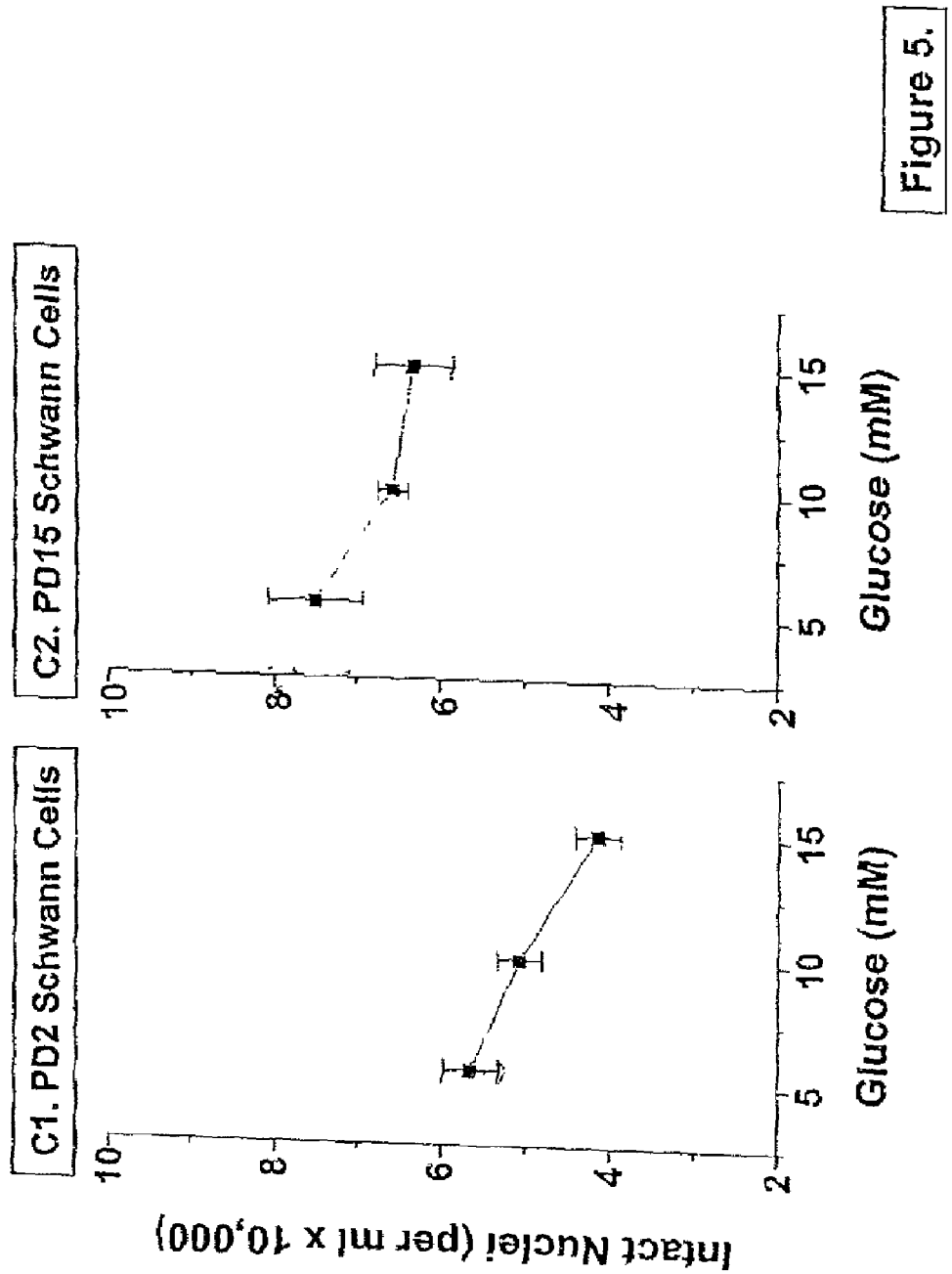

Counts of intact PD2 Schwann cell nuclei following exposure to 5.5, 17.5, 30, 40 and 50 mM glucose media at 0, 2, 12, 24 and 48 hr are shown in FIG. 4A. Each point represents the mean and standard error obtained from 12 individual wells. For all glucose concentrations greater than 5.5 mM an approximate 20% cell loss was observed at 2 hr. This loss does not appear to be dose-dependent. It is not due to the washing of cells just prior to 0 hr since Schwann cells in 5.5 mM glucose media were treated identically and did not display any cell loss at 2 hr. It is possible that there is a vulnerable subset of Schwann cells which may be uniquely sensitive to decreased trophic support due to the reduced serum concentration or to increases in glucose concentrations. Between 2–24 hr, PD2 Schwann cells die in a dose dependent manner with respect to increasing glucose concentrations. Cells in 5.5 mM glucose maintained a constant number of cells. There does not seem to be any significant change in the number of surviving cells at 48 hr as compared to 24 hr as determined by counts of intact nuclei. This would suggest that the rate of PD2 Schwann cell death is greatest in the first 24 hr of exposure to high glucose media.

FIG. 4B shows the glucose dose response curves for counts of intact nuclei from PD15 Schwann cells exposed to 5.5, 17.5, 30, 40 and 50 mM glucose media at 0, 2, 12, 24 and 48 hr. Again, there is an approximate 20% cell loss at 2 hr which appears to be dose dependent for PD 15 cells. Again, washing of cells prior to 0 hr does not appear to be a contributing factor since there was no obvious cell loss at 5.5 mM glucose (compared to counts obtained immediately before washing the cells, data not shown). Between 2–12hr there is a slight increase in the number of cells due to the proliferation of PD 15 cells. Between 12–48hr there is a dose-dependent loss of cells due to increasing glucose concentrations. Cells in 5.5 mM glucose continue to proliferate From these data it would appear that the rate of PD 15 Schwann cell loss is greatest between 12–24 h.

In Situ End-Labeling of Schwann Cells Exposed to High Glucose Media

Figure 6:
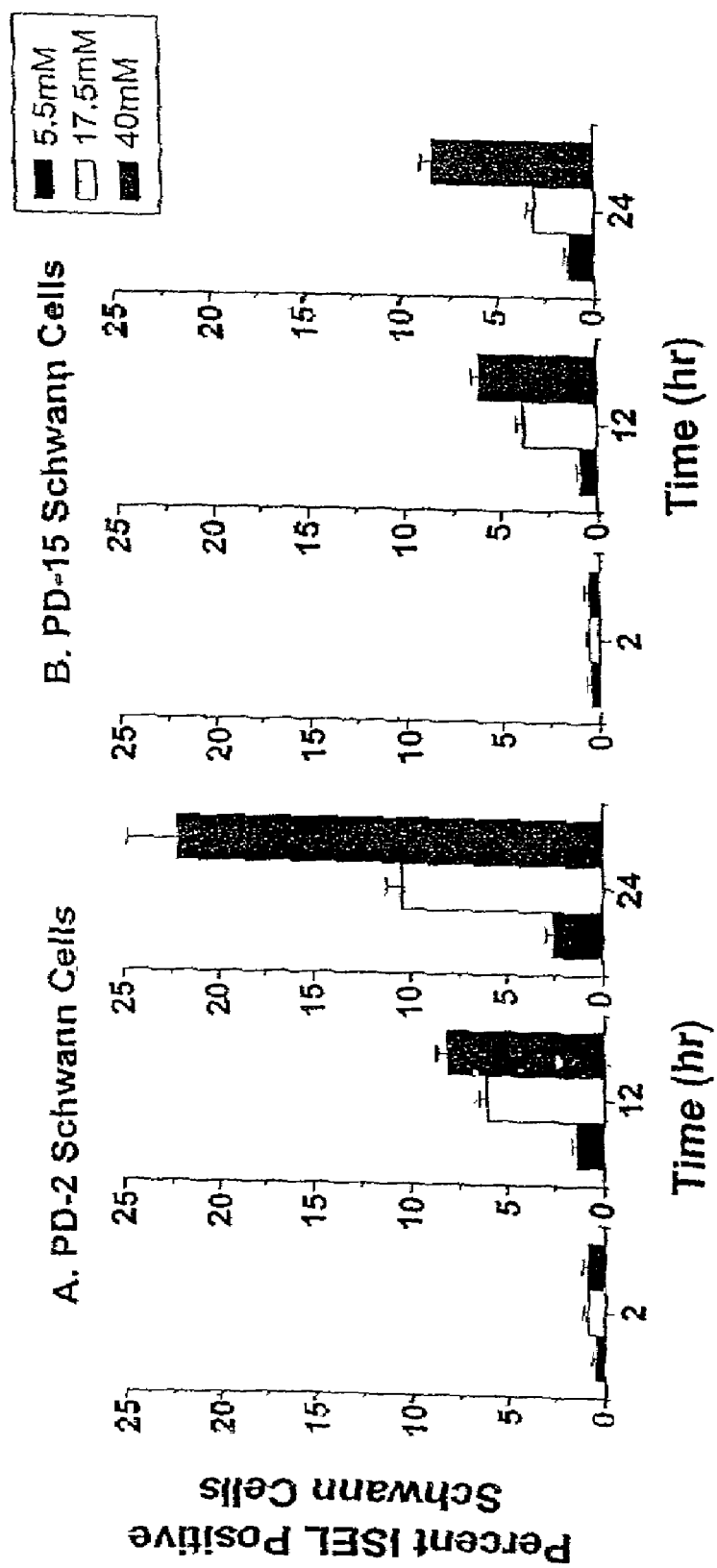
FIG. 6 illustrates the percentage of ISEL positive (+ve) PD2 and PD 15 Schwann cells at 2, 12 and 24 hr in 5.5, 17.5 and 40 mM glucose.

In situ end labeling (ISEL) with terminal deoxynucleotidyl transferase (TdT) was used to detect free 3'-OH ends of cut double-stranded DNA in Schwann cells. The percentage of ISEL positive (+ve) PD2 Schwann cells at 2, 12 and 24hr in 5.5, 17.5 and 40 mM glucose is presented in FIG. 6A and the percentage of ISEL+ve cells in identically treated PD 15 cover slips (n=3 cover slips with approximately 1000 cells counted per cover slip) is presented in FIG. 6B. There was no increase in the number of ISEL+ve cells at 2hr at any glucose concentration for PD2 or PD 15 cells. This would suggest that death observed at this early time point is not apoptotic, however, it must be noted that this method only labels those cells still attached to the cover slips. In order to determine whether any of the cells which have detached died via an apoptotic mechanism it would be necessary to remove the supernatant to recover the floating cells and extract the DNA for agarose gel electrophoresis to determine if there are 'ladders' present indicative of DNA fragmentation. Alternately one could cytospin the cells onto a microscope slide and determine if chromatin condensation characteristic of apoptosis can be observed by epifluorescence of DNA binding dyes. PD2 cells show a dose-dependent increase in the number of ISEL+ve cells over 24 hr in both 17.5 and 40 mM glucose, with approximately 20% of the cells at 24 hr in 40 mM glucose being end-labeled. PD 15 cells also showed a dose dependent increase in the percentage of end-labeled cells at 12 and 24 hr most particularly after exposure to 40 mM glucose. However, the maximum percentage of ISEL+ve cells at 24hr in 40 mM glucose was only about 8%. This may be due to a decreased vulnerability to apoptosis with DNA fragmentation in this population, due in part perhaps to ongoing proliferation. However, apoptotic cell death can occur without apparent DNA fragmentation.

Figure 7:
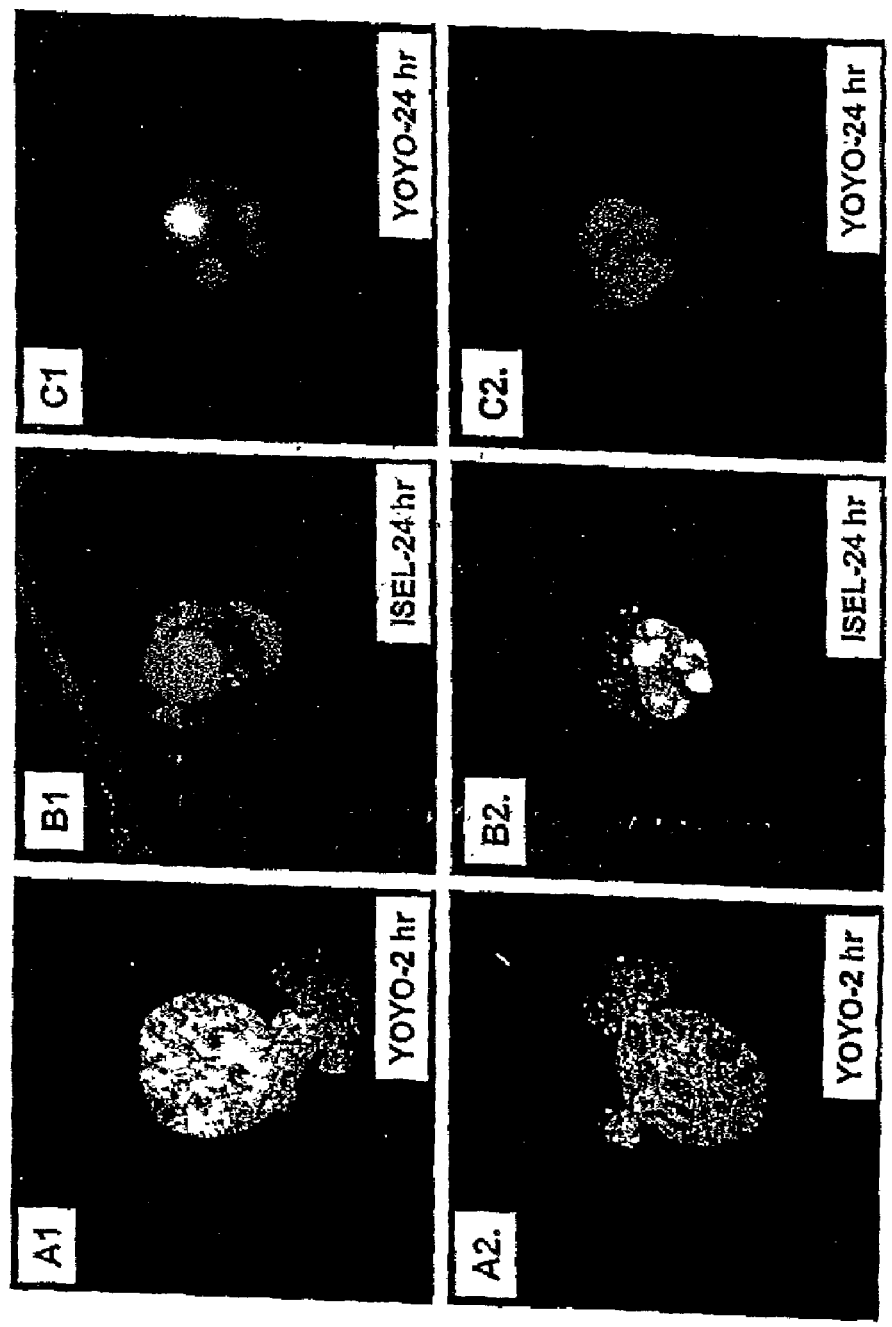
FIG. 7 depicts the appearance of and ISEL positive Schwann cells after exposure to high glucose.

YOYO-1 Reveals Nuclear Blebbing and Chromatin Condensation After High Glucose Exposure The cyanine dye YOYO-1 was used to visualize Schwann cell nuclei after exposure to high glucose. Both PD2 and PD 15 nuclei showed evidence of nuclear blebbing at 2hr (see FIG. 7A1, 7A2). This type of nuclear change is generally found in immunocompetent cells such as lymphocytes or splenocytes. Nuclear blebbing was also observed in cells exposed to high glucose for 24hr (see FIG. 7C1, 7C2) for both PD2 (C1) and PD15 (C2) cells. Their cell plasma membranes did not appear to be irregular, nor did those cells with nuclear blebbing appear to have swollen somata which would be indicative of necrotic changes. This would suggest that there may be a uniquely vulnerable population of Schwann cells which dies via a rapid mechanism during exposure to high glucose levels. Panels 7B1 and 7B2 show ISEL+ve cell nuclei from PD2 and PD15 cultures respectively.

Use of Anti-Apoptotic Agents to Improve Schwann Cell Survival in High Glucose Media Three different agents which have demonstrated anti-apoptotic properties in trophically deprived nerve cells in vitro were used in this model in an attempt to rescue Schwann cells from high glucose induced apoptotic cell death. FIG. 1 presents the percentage of intact nuclei relative to control (5.5 mM glucose) from non-proliferating and proliferating Schwann cells exposed to 40 mM glucose with or without IGF-1 (1 ng/ml), NAC ($10^{-7}$ M), or DMD ($10^{-9}$ M) for 2 or 24 hr. Values plotted are the means plus standard errors of 6–8 wells. At 2 hr there is a significant increase in the number of cells treated with IGF-1, NAC and DMD for both non-proliferating and proliferating cells exposed to 40 mM glucose. At 24 hr the rescue effect of these agents is even more pronounced. Between 80 and 95% percent of apoptotic cells are rescued in the non-proliferating group; while 60–100% of apoptotic cell death is prevented in the non-proliferating group.

Changes in Schwann Cell $\Delta\Psi M$ in High Glucose Media

It has been demonstrated in two different in vitro model systems that a reduction in $\Delta\Psi M$ occurs prior to any observable nuclear changes such as ISEL or condensed chromatin. The potentiometric dye CMTMR was utilized to label Schwann cell mitochondria in order to determine whether a drop in $\Delta\Psi M$ was associated with the observed cell loss following exposure to high glucose. FIG. 8 illustrates confocal laser microscopic images of CMTMR dye in PD2 cells after 6hr exposure in each of the listed media. Note the bright fluorescent labeling of mitochondria observed in Schwann cells in 5.5 mM base media (FIG. 8A) in contrast with the low CMTMR observed in cells treated with 40 mM glucose (8B) or trophically withdrawn (serum-free=M/O) cells (8C). Cells treated with $10^{-9}$ M DMD and 40 mM glucose (8D) showed comparable levels of CMTMR fluorescent intensity compared with cells in base media and significantly greater intensity than that displayed by cells treated with 40 mM glucose alone. Similarly, cells treated with CsA and 40 mM glucose (8E) showed enhanced brightness compared with cells in 40 mM glucose only. Cells treated with 40 mM glucose and ATR (8F), which opens the PTP, showed decreased CMTMR brightness compared with cells in 5.5 and 40 mM glucose.

Figure 9:
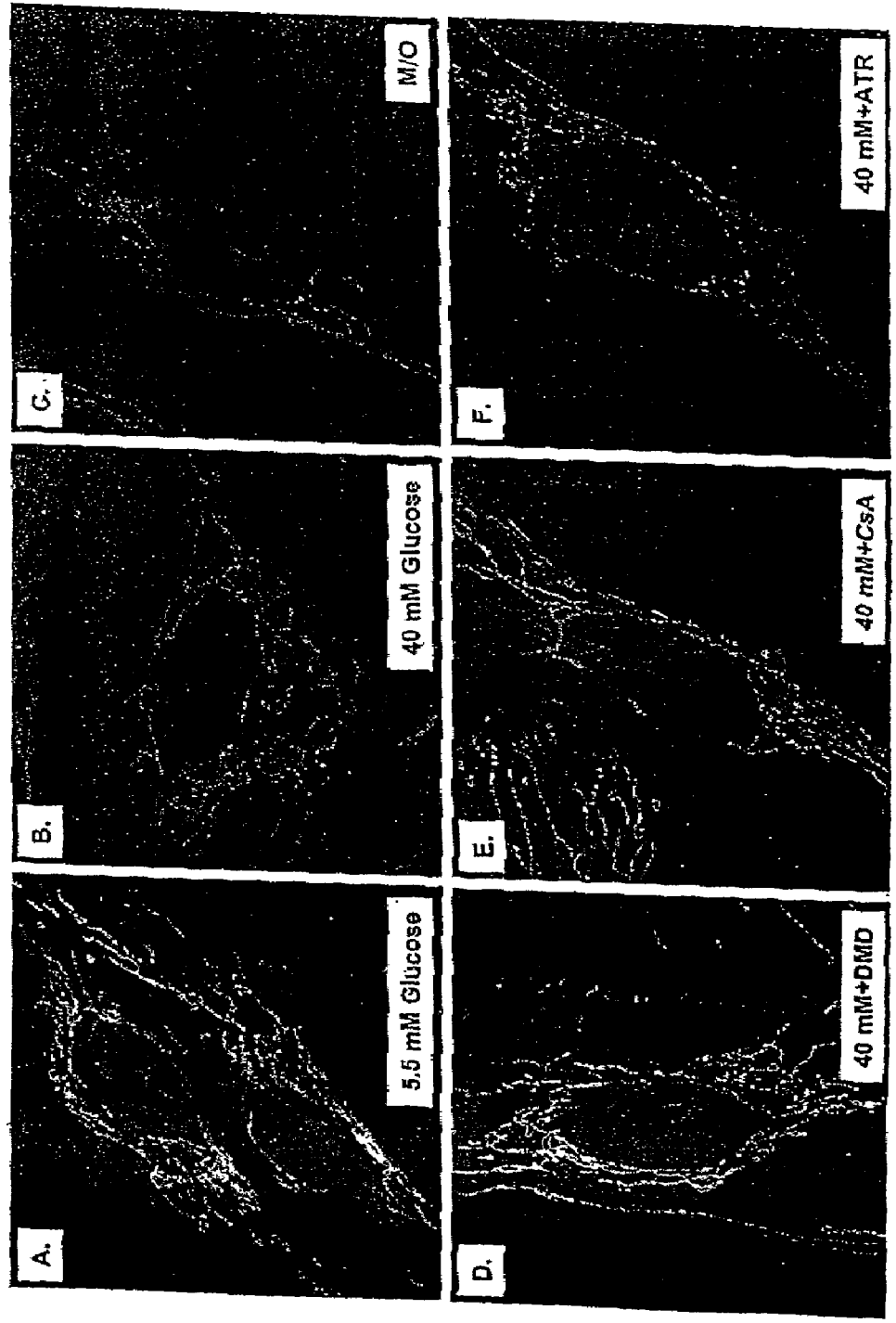
FIG. 9 displays the corresponding distribution frequencies of ΔΨM in PD2 Schwann cells exposed for 6 h to base media alone, 40 mM glucose and M/O cells.
Figure 9:
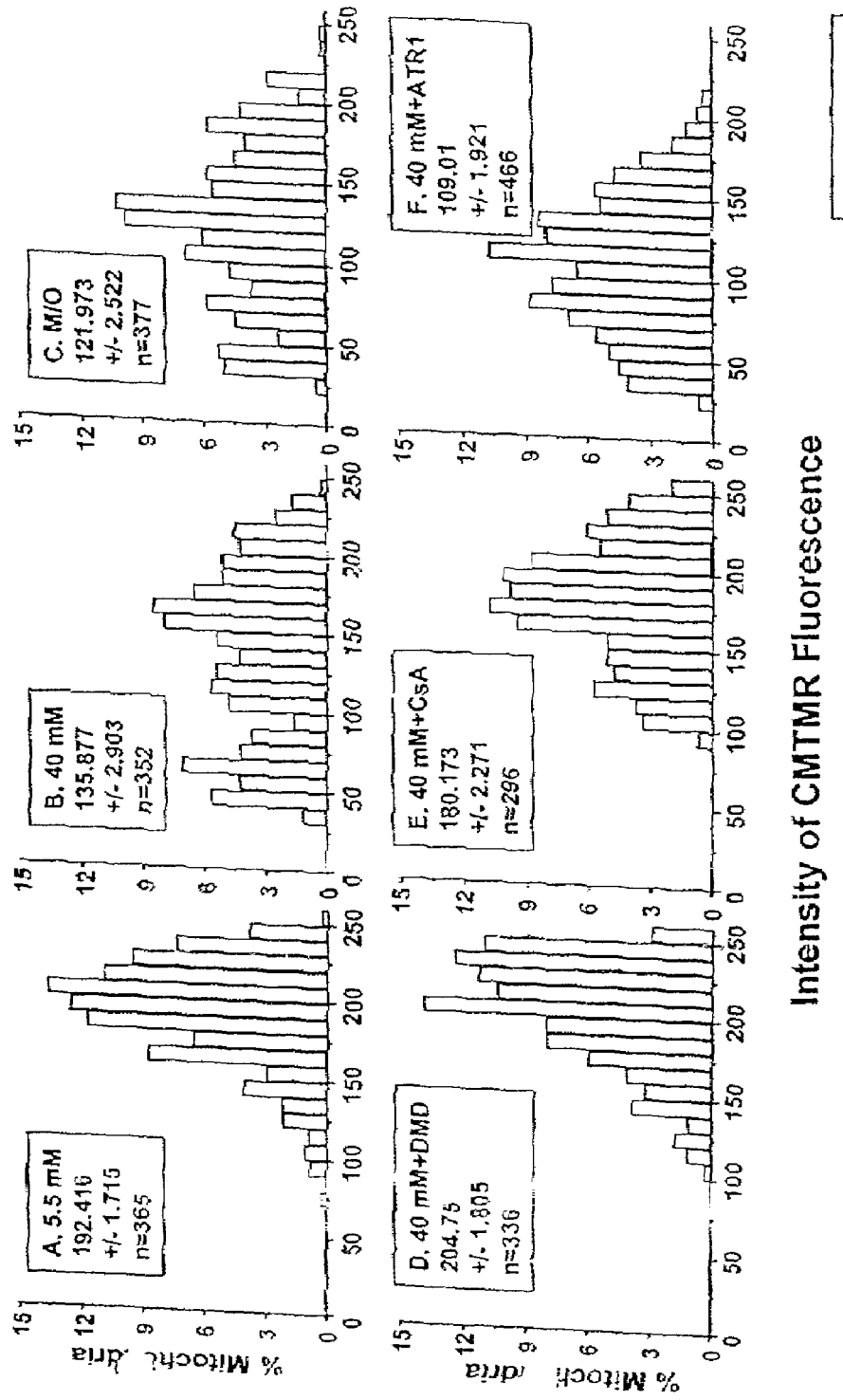

FIG. 9 displays the corresponding distribution frequencies of $\Delta\Psi M$ in PD2 Schwann cells exposed for 6 h to base media alone (FIG. 9A), 40 mM glucose (9B) and M/O cells (9C) in the upper panel. The lower panel depicts the distributions for cells treated with 40 mM glucose+$10^{-9}$ M DMD (9D), 40 mM glucose+$10^{-7}$ CsA (9E) and 40 mM glucose+1 mM ATR (9F). CMTMR intensity measurements were taken initially from a minimum of 10 cells per group with 30 to 40 individual mitochondria sampled from within each cell. There is a notable shift of the distribution to the left, indicating a decrease in the $\Delta\Psi M$ in cells treated with 40 mM glucose compared with cells in 5.5 mM glucose. Also note that there is an overall decrease in percentage of mitochondria displaying high CMTMR intensity levels. Similarly, there is a similar shift to the left in trophically withdrawn (M/O) cells. Schwann cells treated with 40 mM glucose and DMD have restored $\Delta\Psi M$ distributions comparable with the base media. CsA treated cells exposed to 40 mM glucose also show a shift back to the right, while cells treated with 40 mM glucose+ATR demonstrated a pronounced shift to the left.

These data suggest that the agents DMD and CsA help maintain $\Delta\Psi M$ in Schwann cells exposed to high glucose for 6 h. Previous studies in PC12 cells have demonstrated that maintenance of the $\Delta\Psi M$ is correlated to cell survival in trophically withdrawn cells. The simultaneous treatment of Schwann cells with 40 mM glucose and the PTP opening agent ATR (1 mM) further left-shifted the CMTMR distribution induced by high glucose alone. However Schwann cells cultured in base media (5.5 mM glucose) exposed to the same dose of ATR showed a similar distribution of CMTMR intensity (data not shown), suggesting that the drop in $\Delta\Psi M$ elicited by exposure to 40 mM glucose for 6 hr did not potentiate the effect of ATR.

Production of NO in Schwann Cells in High Glucose Media

To determine the role of NO signaling in high glucose induced Schwann cell apoptosis, PD2 and PD15 Schwann cells were cultured, as described, in the presence of 5.5 or 40 mM glucose for 24 hr. Cells exposed to 40 mM glucose were also treated with DMD ($10^{-9}$ M), the iNOS inhibitor L-NIL ($10^{-4}$ M) or an inhibitor of the constitutive, Ca++-dependent isoform of NOS (cNOS), S-methyl-thiocitruline (SMTC, $10^{-4}$M). As an internal positive control during the high glucose experiments, Schwann cells in normal base media were treated with TNF-α/IFN-y (100U), which has been shown to increase the production of NO in Schwann, cells in vitro. PD2 Schwann cells were also treated with increasing amounts of TNF-α22 plus IFN-γ (50, 100, 250, and 500U) for 24 hr to establish a dose-response threshold for the assay.

Figure 10:
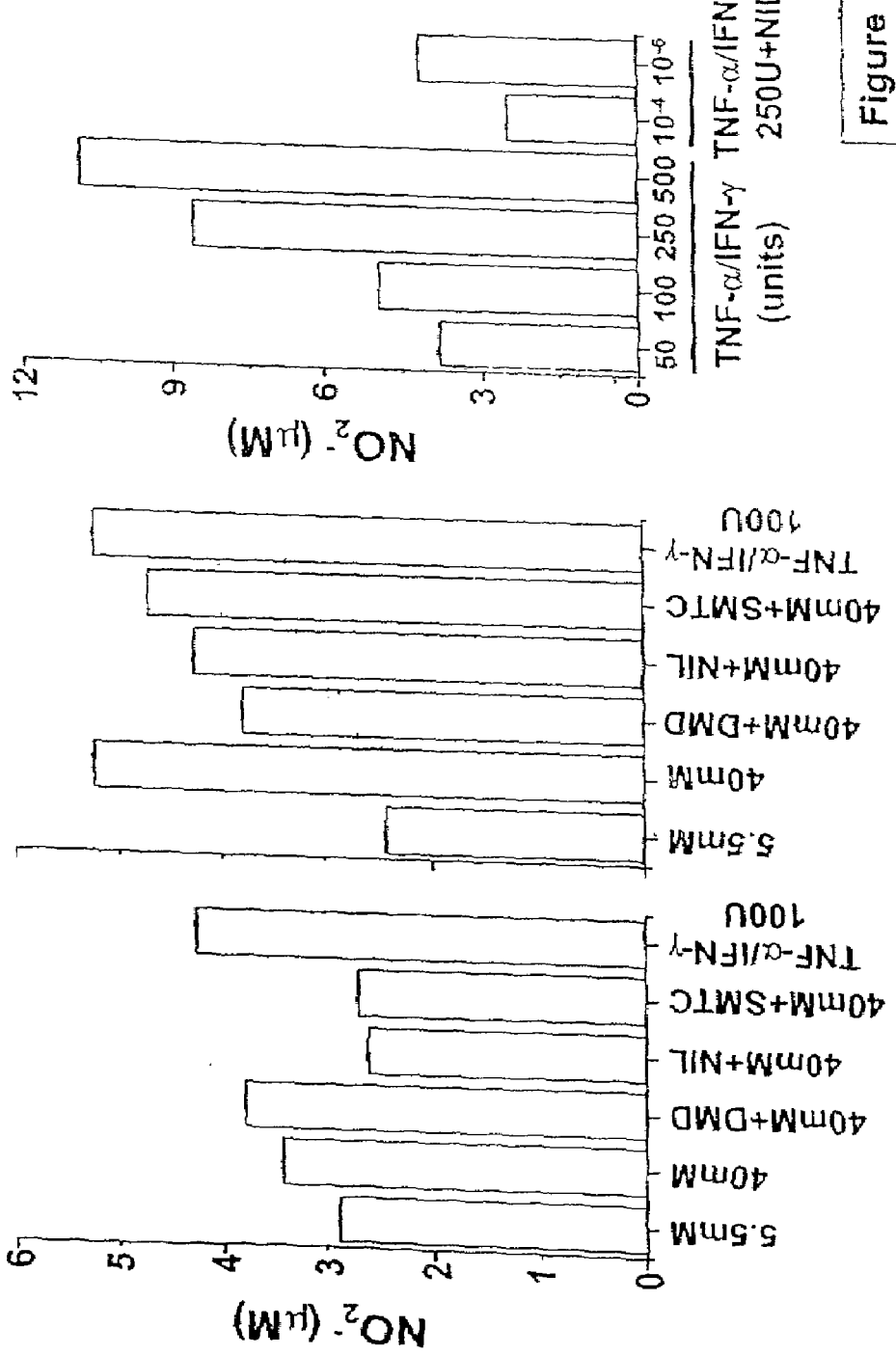
FIG. 10 shows the levels of NO₂ production by Schwann cells exposed to high glucose or TNF-α/IFN-γ.

The Griess reaction, which measures secreted nitrite ($NO_2$) in the culture medium, was used to investigate NO production by Schwann cells. FIG. 10A1 shows the levels of $NO_2$ in the media of PD2 cells exposed to high glucose. The amount of detected $NO_2$ was not significantly different in Schwann cells exposed to 40 mM glucose compared to 5.5 mM glucose at 24 hr. In PD 15 Schwann cells, however, the was a significant increase in $NO_2$ levels in Schwann cells exposed to 40 mM glucose for 24 hr (FIG. 10A2). DMD, as well as L-NIL, treatment in Schwann cells exposed to high glucose resulted in a slight decrease in $NO_2$ production.

Treatment of PD2 Schwann cells with TNF-a/IFN-γ (50, 100, 250, 500U) resulted in a dose-dependent production of NO to almost 4 fold above control levels in 5.5 mM glucose (FIG. 10B) providing upper and lower sensitivity limits of the current assay conditions and indicating the capacity of Schwann cells to upregulate NO production. Stimulation of $NO_2$ release by TNF-a/IFN-γ was prevented by addition of the iNOS inhibitor L-NIL.

Discussion

Survival of PD2 and PD15 Schwann Cells in High Glucose Media

Using counts of intact nuclei as a measure of cell survival, high glucose is toxic to pure populations of PD2 and PD15 Schwann cells. This glucose-induced cell death was dose-dependent at concentrations between 17.5 mM and 50 mM.

Characteristic features of late stage apoptosis are condensed chromatin and internucleosomal fragmentation of DNA by activated endonucleases. DNA fragmentation and chromatin condensation can be detected in situ providing a marker for apoptotic cells. The free 3'-OH ends of cut DNA are enzymatically labeled with fluorophore-tagged oligonucleotides allowing visualization of apoptotic nuclei. In addition, nucleic acid specific stains such as YOYO-1, propidium iodide, and Hoescht 33258 can be utilized to demonstrate "clumping" or condensation of the chromatin. It has recently been suggested that TdT-mediated ISEL may also mark necrotic cells, leading to the overestimation of the extent of apoptosis. To address this concern it is therefore necessary to utilize several independent markers of apoptosis in addition to ISEL, such as visualization of chromatin condensation, the presence of DNA "ladders" on gel electrophoresis, or the spectrofluorometric quantification of small fragmented DNA that has been purified from intact genomic DNA. In the present study fragmentation of nuclear DNA (by ISEL) and condensation of chromatin (by the nucleic acid specific dye YOYO-1) in Schwann cells exposed to high glucose conditions was observed.

In the present study, both PD2 and PD15 Schwann cells were ISEL positive following exposure to high glucose media. The cyanine dye YOYO-1 revealed the presence of chromatin condensation as observed with laser confocal microscopy, confirming that these cells were indeed apoptotic. Interestingly, there was a significant loss of cells within 2 hr of exposure to elevated glucose levels. These cells were not ISEL positive but did demonstrate nuclear blebbing which has been observed in the apoptotic cell death of lymphocytes exposed the respiratory chain inhibitors rotenone, antimycin A, and the ATP synthase inhibitor oligomycin.

Acute exposure to high glucose conditions may disrupt attachment of the Schwann cells to the plastic substrate. It has been demonstrated that hyperglycemia induced by streptozotocin impairs the subsequent attachment of isolated dorsal root ganglion (DRG) neurons in vitro. Further, as described above, incubation of non-diabetic explant preparations of rabbit tibial nerve in high glucose containing medium did not alter endoneurial metabolism during a 2 hr incubation period, suggesting that the cell loss observed during the initial 2 hr may not be the result of metabolic processes leading to cell death.

Schwann cell survival was significantly improved by the addition of IGF-I, NAC, and DMD to the high glucose media. In the present study the co-administration of IGF-I, NAC, or DMD simultaneously with 40 mM glucose reduced the amount of Schwann cell death. The protective effect at 2 hr suggests that new protein synthesis may not be a requirement for those dying cells that did not display DNA fragmentation.

Reduction in ΔΨM in Schwann Cells Exposed to High Glucose

Given the importance of mitochondrial signaling in several apoptotic systems (see above), and the determination that Schwann cells were dying by an apoptotic mechanism when exposed to high glucose, an analysis of changes in 6 hr in Schwann cells exposed to high glucose was undertaken. It was shown that exposure of PD2 Schwann cells to 40 mM glucose for 6 hr resulted in a significant shift in the distribution of CMTMR fluorescence intensity toward the left compared to cells grown in 5.5 mM glucose, indicating a drop in ΔΨM. Similarly, a shift to the left in the distribution of CMTMR intensity was also found in trophically withdrawn Schwann cells. The apoptotic cell death of Schwann cells here was shown to be prevented by the addition of DMD to the high glucose media. (−)Deprenyl, the parent molecule of DMD has been shown in several systems to reduce the apoptotic death of neuronal and non-neuronal cells, prevent the trophic withdrawal induced drop in ΔΨM in PC12 cells, and the AraC induced drop in ΔΨM in cultured cerebellar granule cells. It was shown here that addition of DMD to high glucose media prevented the shift to the left of the distribution of CMTMR intensity.

Conclusions

The anti-apoptic compounds NAC, IGF-I, and DMD improved the survival of Schwann cells when simultaneously added with 40 mM glucose. Also, ΨM is significantly reduced by 6 hr in PD2 Schwann cell exposed to 40 mM glucose or trophic withdrawal, and that this reduction is prevented by the addition of DMD or the PTP-closing agent CsA; also, the PTP opening agent, ATR caused a significant drop in ΔΨM, in both normal glucose and high glucose.

Example 2

Sprague-Dawley rats, aged 5 weeks were injected with streptozotocin (STZ), 65 mg/kg i.p., or vehicle. One group were given (−)-deprenyl (0.1 mg/kg) on alternate days, beginning 72 h after the STZ injection. Rats were perfused and sciatic nerves removed for histology or decapitated and sciatic nerves removed for RNA extraction. Animals were examined at 2 and 3 weeks after STZ injection.

FIG. 11 shows in situ end-labeled nuclei (using the ApopTag kit) from cryosections through the sciatic nerve (A). Sections through the cortex of a 4 day old kitten served as positive controls of programmed apoptotic cell death. Note that in the sciatic nerve, Schwann cell nuclei were labeled while in the spinal cord both the nucleus and the cell body of some neurons were end-labeled. These 2 types of end-labeling have also been observed in programmed cell death in development (see arrows, FIG. 11B.)

Figure 12:
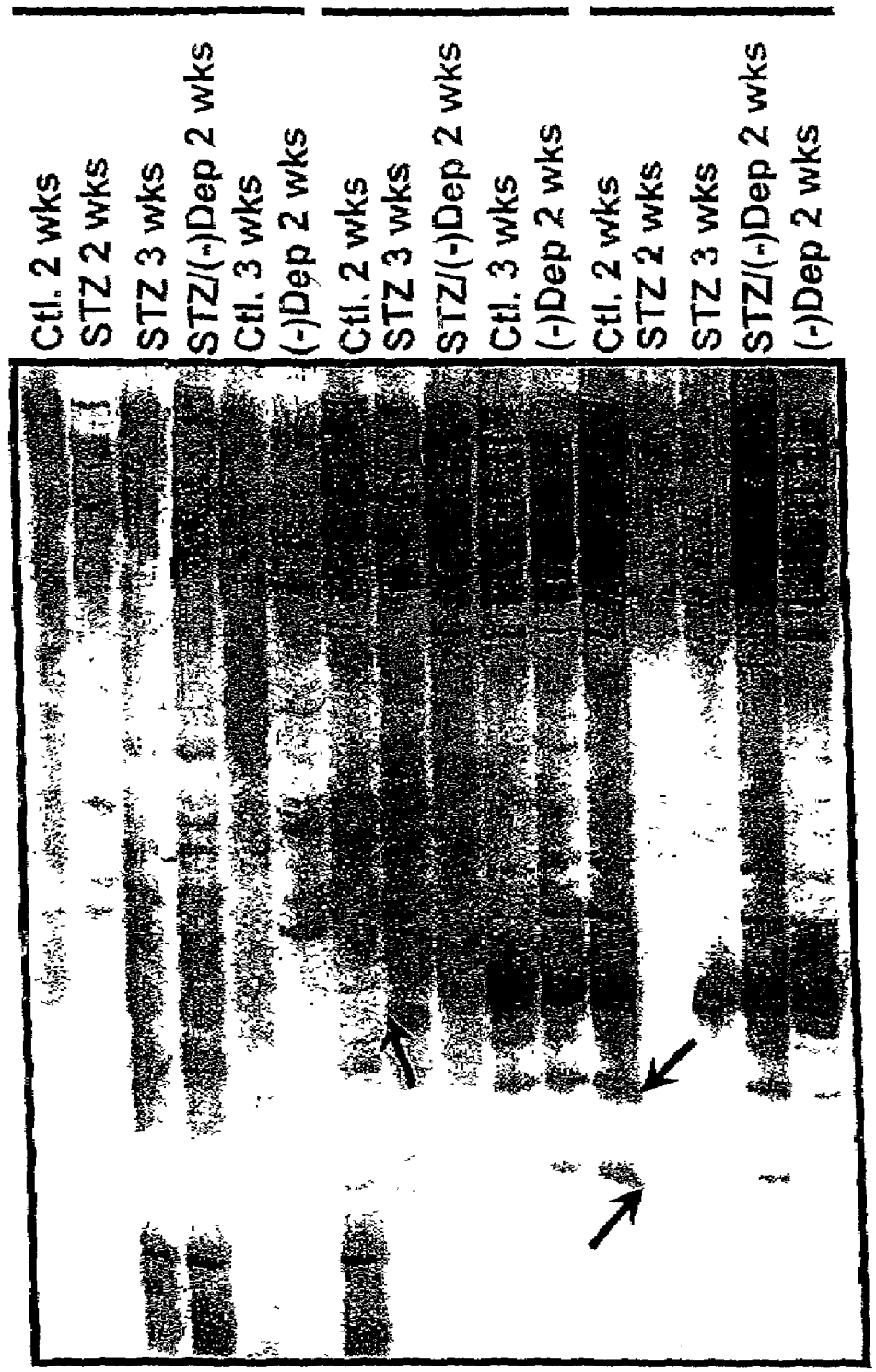
FIG. 12 shows differential display PCR of rat RNA taken from sciatic nerves pooled from four rats, as further detailed in Example 2.

FIG. 12 shows differential display PCR (DDPCR) of rat RNA taken sciatic nerves pooled from four rats. A commercially available kit was used and lanes grouped according to the 3' base primers. Although not confirmed with Northern blots to demonstrate true positive bands, the data suggests that not only does STZ treatment result in new gene expression in the sciatic nerve, but this may be modulated by (−)-deprenyl treatment.

Equivalents

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed is:

1. A method for increasing survival of Schwann cells, comprising administering an effective amount of a compound selected from the group consisting of a deprenyl compound, N-acetyl cysteine and IGF-1, to a patient such that survival of Schwann cells is increased.

2. The method of claim 1, wherein the deprenyl compound is represented by the structure:

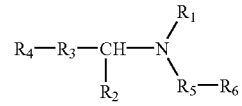

in which $R_1$ is hydrogen, alkyl, alkenyl, alkynyl, aralkyl, alkylcarbonyl, arylcarbonyl, alkoxycarbonyl, or aryloxycarbonyl;

$R_2$ is hydrogen or alkyl;

$R_3$ is a single bond, alkylene, or

—(CH$_2$)$_n$—X—(CH$_2$)$_m$;

in which X is O, S, or N-methyl; m is 1 or 2; and n is 0, 1, or 2;

$R_4$ is alkyl, alkenyl, alkynyl, heterocyclyl, aryl or aralkyl; and $R_5$ is alkylene, alkenylene, alkynylene and alkoxylene; and $R_6$ is C$_3$–C$_6$ cycloalkyl or —C≡CH; or $R_2$ and $R_4$–$R_3$ are joined to form, together with the methine to which they are attached, a cyclic or polycyclic group;

and pharmaceutically acceptable salts thereof.

3. The method of claim 2, wherein $R_1$ is a group that can be removed in vivo.

4. The method of claim 2, wherein $R_1$ is hydrogen.

5. The method of claim 2, wherein $R_1$ is alkyl.

6. The method of claim 2, wherein $R_1$ is methyl.

7. The method of claim 2, wherein $R_2$ is methyl.

8. The method of claim 2, wherein $R_3$ is methylene.

9. The method of claim 2, wherein $R_4$ is aryl.

10. The method of claim 2, wherein $R_4$ is phenyl.

11. The method of claim 2, wherein $R_5$ is methylene.

12. The method of claim 2, wherein $R_6$ is

—C≡CH.

13. The method of claim 2, wherein the deprenyl compound is represented by the structure:

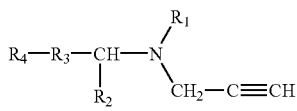

in which
R₁ is hydrogen, alkyl, alkenyl, alkynyl, aralkyl, alkylcarbonyl, arylcarbonyl, alkoxycarbonyl, or aryloxycarbonyl;
$R_2$ is hydrogen or alkyl;
$R_3$ is a bond or methylene; and
$R_4$ is aryl or aralkyl; or
$R_2$ and $R_{4-R_3}$ are joined to form, together with the methine to which they are attached, a cyclic or polycyclic group;
and pharmaceutically acceptable salts thereof.

14. The method of claim 2, wherein the deprenyl compound is represented by the structure:

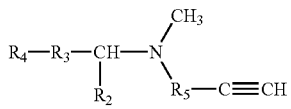

in which
$R_2$ is hydrogen or alkyl;
$R_3$ is a bond or methylene; and
$R_4$ is aryl or aralkyl; or
$R_2$ and $R_4$–$R_3$ are joined to form, together with the methine to which they are attached, a cyclic or polycyclic group; and
$R_5$ is alkylene, alkenylene, alkynylene and alkoxylene; and pharmaceutically acceptable salts thereof.

15. The method of claim 2, wherein the deprenyl compound is represented by the structure:

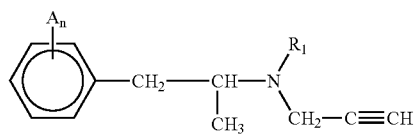

in which
R₁ is hydrogen, alkyl, alkenyl, alkynyl, aralkyl, alkylcarbonyl, arylcarbonyl, alkoxycarbonyl, or aryloxycarbonyl;
A is a substituent independently selected for each occurence from the group consisting of halogen, hydroxyl, alkyl, alkoxyl, cyano, nitro, amino, carboxyl, —$CF_3$, or azido;
n is 0 or an integer from 1 to 5;
and pharmaceutically acceptable salts thereof.

16. The method of claim 1, wherein said patient is a human.

17. The method of claim 1, wherein said deprenyl compound is (−)-desmethyldeprenyl.

18. A method for inhibiting peripheral neuropathy, comprising administering to a patient an effective amount of a compound selected from the group consisting of a deprenyl compound, N-acetyl cysteine and IGF-1, such that peripheral neuropathy is inhibited.

19. The method of claim 18, wherein said deprenyl compound is (−)-desmethyldeprenyl.

20. The method of claim 18, wherein said neuropathy is selected from the group consisitng of diabetic neuropathy and AIDS-related neuropathy.

21. The method of claim 18, wherein said patient is a human.

22. A method for increasing Schwann cell survival in a patient, comprising contacting a Schwann cell with a compound selected from the group consisting of a deprenyl compound, N-acetyl cysteine and IGF-1, such that Schwann cell survival increases.

23. The method of claim 22, wherein said patient is a human.

24. The method of claim 22, wherein the deprenyl compound is (−)-desmethyldeprenyl.

25. The method of claim 24, wherein the (−)-desmethyldeprenyl is administered transdermally to the patient.

26. A method for treating peripheral neuropathy, comprising administering to a patient an effective amount of a compound selected from the group consisting of a deprenyl compound, N-acetyl cysteine and IGF-1, such that peripheral neuropathy is treated.

* * * * *